United States Patent
Choi et al.

(10) Patent No.: US 10,292,620 B1
(45) Date of Patent: May 21, 2019

(54) STEREO IMAGING ACQUISITION BY LENS TRANSLATION

(71) Applicants: Wook Choi, Los Angeles, CA (US); Vladimir Rubtsov, Los Angels, CA (US); Chang-Jin Kim, Beverly Hills, CA (US); Gennady Sigal, Oakville (CN)

(72) Inventors: Wook Choi, Los Angeles, CA (US); Vladimir Rubtsov, Los Angels, CA (US); Chang-Jin Kim, Beverly Hills, CA (US); Gennady Sigal, Oakville (CN)

(73) Assignees: THE REGENTS OF THE UNIVERSITY OF CALIFORNIA, Oakland, CA (US); OPTECH VENTURES, LLC, Torrence, CA (US)

( * ) Notice: Subject to any disclaimer, the term of this patent is extended or adjusted under 35 U.S.C. 154(b) by 1071 days.

(21) Appl. No.: 13/737,914

(22) Filed: Jan. 9, 2013

Related U.S. Application Data

(60) Provisional application No. 61/585,124, filed on Jan. 10, 2012.

(51) Int. Cl.
*A61B 1/00* (2006.01)
*A61B 5/06* (2006.01)
*H04N 13/211* (2018.01)
*A61B 5/00* (2006.01)

(52) U.S. Cl.
CPC .......... *A61B 5/061* (2013.01); *A61B 1/00002* (2013.01); *A61B 5/00* (2013.01); *H04N 13/211* (2018.05)

(58) Field of Classification Search
CPC ...................................................... A61B 90/10
See application file for complete search history.

(56) References Cited

U.S. PATENT DOCUMENTS

| | | | | |
|---|---|---|---|---|
| 6,144,762 | A * | 11/2000 | Brooks | G02B 21/22 348/E13.007 |
| 2001/0037064 | A1 * | 11/2001 | Shahidi | A61B 90/10 600/429 |
| 2011/0051212 | A1 * | 3/2011 | Rolland | A61B 5/0066 359/212.2 |

* cited by examiner

*Primary Examiner* — Joseph M Santos Rodriguez
(74) *Attorney, Agent, or Firm* — Lawrence S. Cohen

(57) ABSTRACT

A stereo-imaging device that operates by translating a single lens in front of an exposed imaging sensor, or translating one of the objective lens group for higher image quality. The device and method is used as a surgical instrument guide. An objective lens with a translating lens part can directly attached in front of a camera with an exposed sensor or an endoscopic circuit with an exposed imaging fiber bundle surface to capture/record the image shift generated by the lens translation. The stereo-imaging device can realize a camera which can swing back and forth from regular 2D image capturing mode to the stereo mode to capture images for 3D viewing, or a switchable stereo endoscope without size increases of multiple imaging systems to be used for periodical 3D inspections.

21 Claims, 22 Drawing Sheets

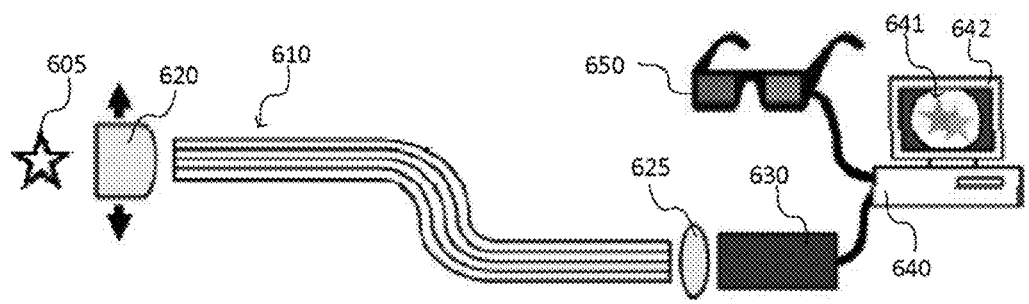
FIG. 6
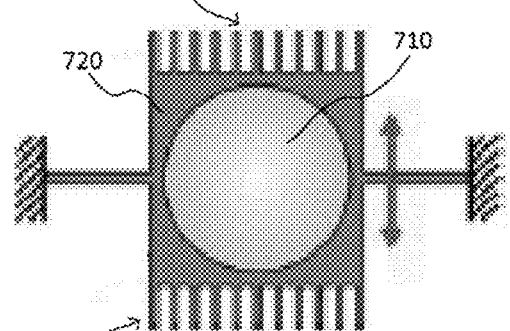
FIG. 7
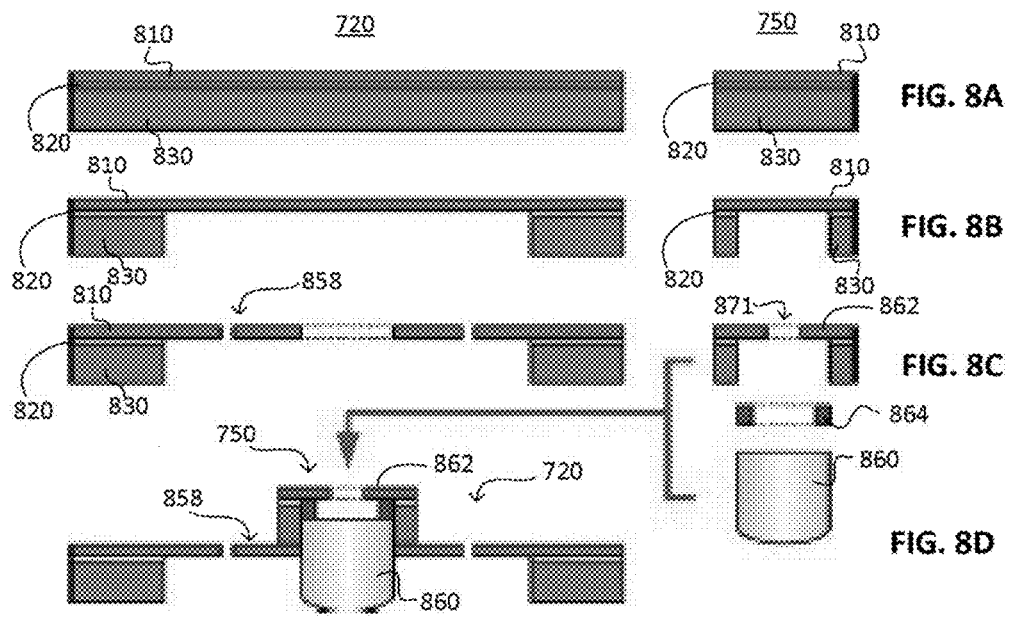
FIG. 8A
FIG. 8B
FIG. 8C
FIG. 8D

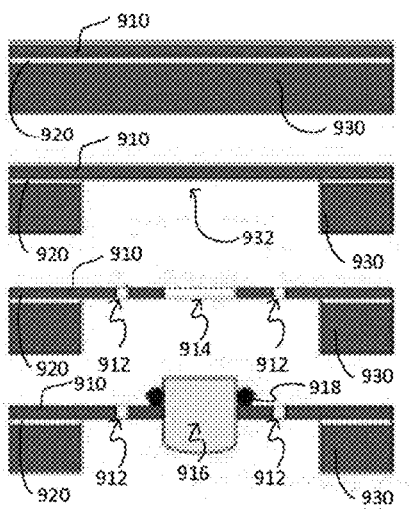
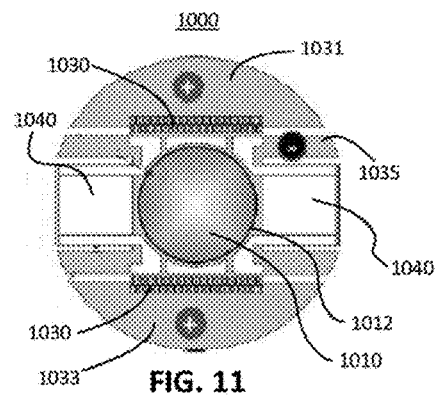
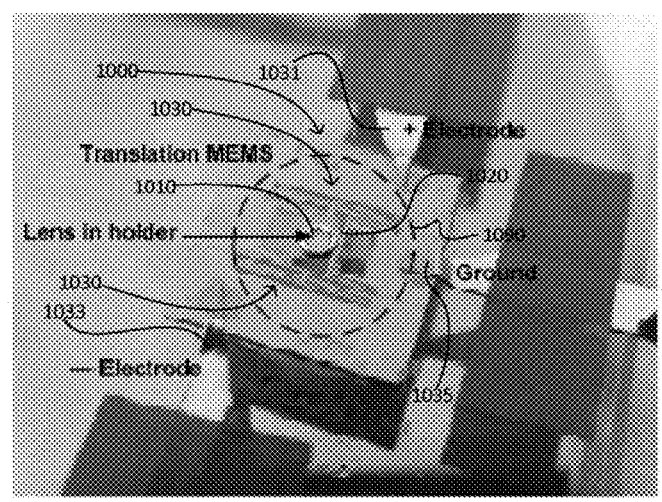
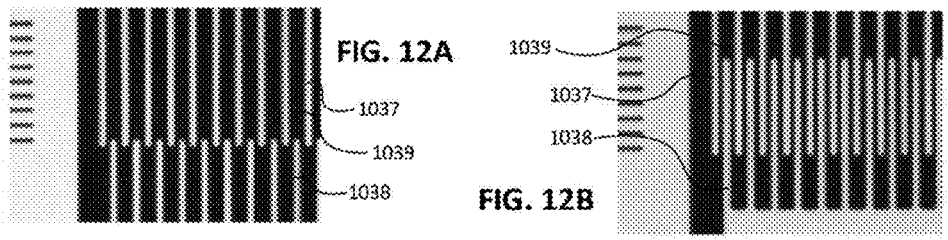
FIG. 9A
FIG. 9B
FIG. 9C
FIG. 9D
FIG. 10
FIG. 11
FIG. 12A
FIG. 12B

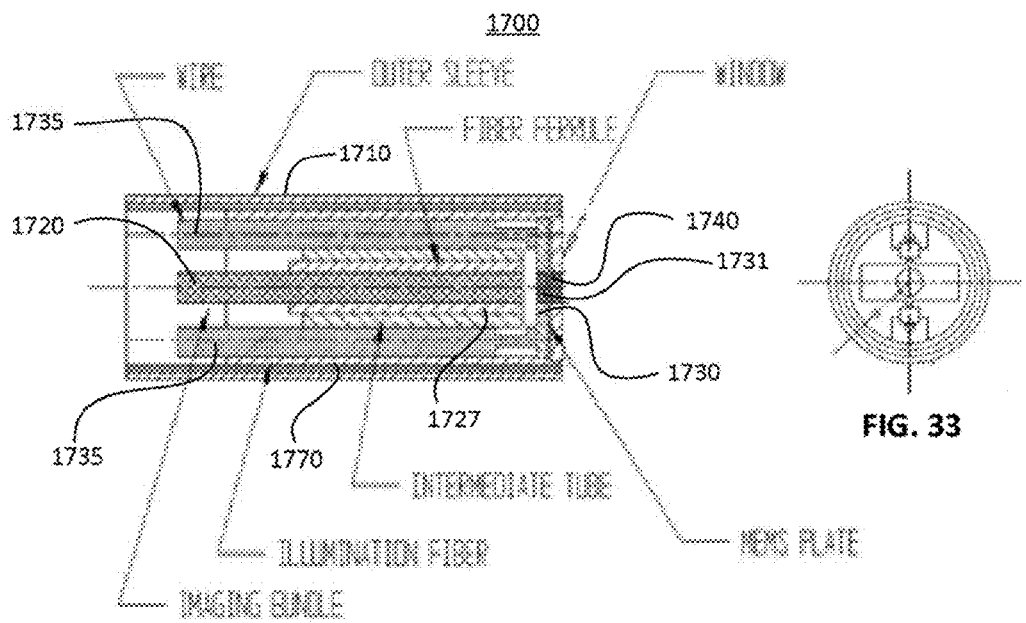
FIG. 17
FIG. 33
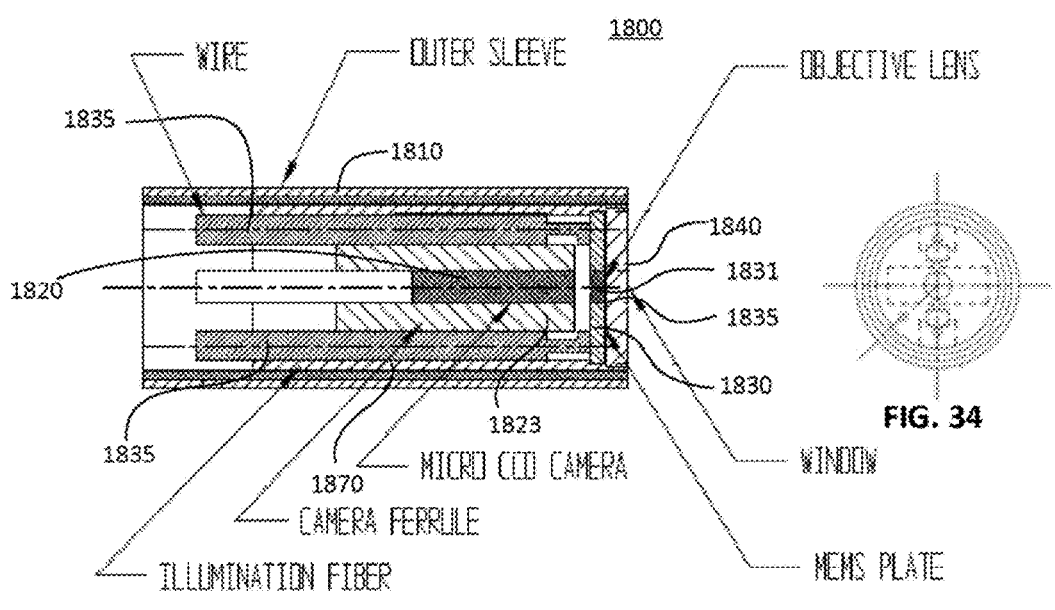
FIG. 18
FIG. 34

Aperture Stop with Lens are shifted for 100 microns.
The image Plane Position corresponds the optimal one for Object Distance 10mm.

| Object to Aperture Stop Distance, mm | Chief Ray of On-Axis Field Y- Sift on Image plan, microns |
|---|---|
| 2 | 125.6 |
| 3 | 117.1 |
| 4 | 112.8 |
| 5 | 110.3 |
| 6 | 108.6 |
| 7 | 107.3 |
| 8 | 106.4 |
| 9 | 105.7 |
| 10 | 105.1 |
| 11 | 104.7 |
| 12 | 104.3 |
| 13 | 103.9 |
| 14 | 103.7 |
| 15 | 103.4 |
| 16 | 103.2 |
| 17 | 103.0 |
| 18 | 102.8 |
| 19 | 102.7 |
| 20 | 102.6 |

FIG. 28D

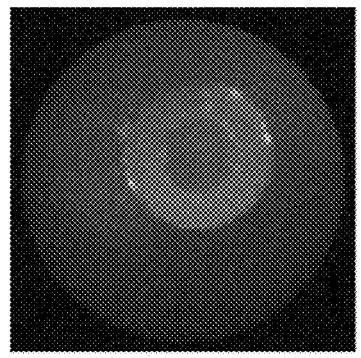
FIG. 36B
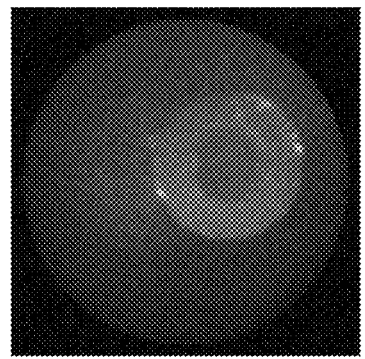
FIG. 36C
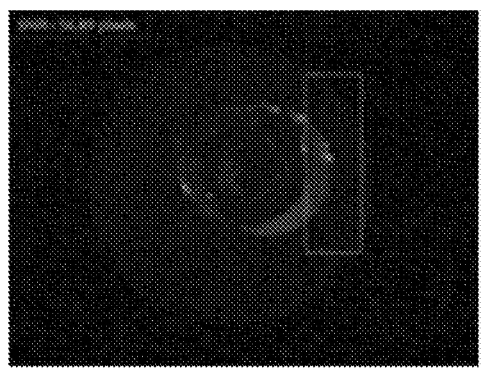
FIG. 36D
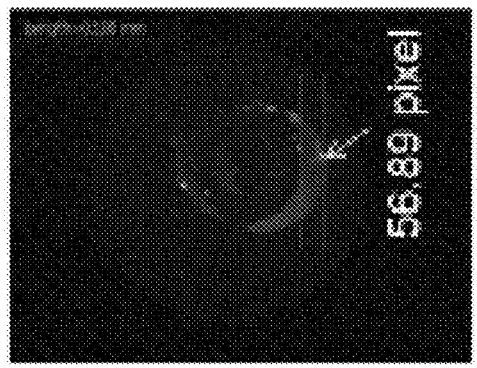
FIG. 36E
FIG. 36F

STEREO IMAGING ACQUISITION BY LENS TRANSLATION

CROSS-REFERENCE TO RELATED APPLICATIONS

The present application is related to and claims the benefit of U.S. Provisional Patent Application No. 61/585,124, titled "Stereo Image Acquisition by Lens Translation for Surgical Instrument and System and Method," filed on Jan. 10, 2012, which is incorporated herein by reference in its entirety.

STATEMENT REGARDING FEDERALLY SPONSORED RESEARCH OR DEVELOPMENT

The invention described herein was made under one or more of contracts from the National Institutes of Health contract nos. 1R43RR030712-01 and 1R43-DK085783-01. The Government may have rights under this invention.

BACKGROUND

1. Field

This disclosure relates to devices, systems, and methods for generating three dimensional images.

2. Description of Related Art

Advances in laparoscopy, as well as accomplishments in computer science and image and signal processing, have resulted in computer assisted surgery, a new advanced surgical approach. As with earlier methods, this approach requires many new tools and procedures. Further evolution in less invasive surgery has led to minimum or scarless surgical procedures, known as laparoendoscopic single-site surgery (LESS) and natural orifice transluminal endoscopic surgery (NOTES). In the LESS approach, only one incision, about 15 mm, is required, and all tools are delivered through a multichannel trocar secured in this single port. A vast improvement over more traditional laparoscopic surgery and even LESS, NOTES uses natural orifices for access to the abdominal viscera. From an instrumental point of view, the NOTES approach can be viewed as a logical continuation of LESS. Progress of the LESS and NOTES techniques has prompted the development of various instrumentation with many more advanced features than those of traditional endoscopic and laparoscopic equipment.

SUMMARY

Described herein are devices, apparatus, methods and systems according to embodiments of the present invention that provide for stereo imaging.

More particularly, the present disclosure describes the use of a translating lens unit to provide multiple images of a viewed object or area, where the multiple images may be used to create a three dimensional image or to determine a distance to an object or area. A particular application of the disclosed devices, systems, and methods is to support endoscopic and laparoscopic surgical procedures.

A first embodiment is a translating lens apparatus for imaging an object comprising: a translating lens; a lens holder mechanically coupled to the translating lens, wherein the lens holder is configured to move bilaterally; an actuating apparatus mechanically coupled to the lens holder, wherein the actuating apparatus is configured to move the lens holder in a first lateral direction to a first maximum extent and to move the lens holder in a second lateral direction opposite to the first lateral direction to a second maximum extent; and an imaging apparatus receiving light directed through the translating lens, wherein the imaging apparatus is configured to capture a first image when the lens holder is at the first maximum extent and to capture a second image when the lens holder is at the second maximum extent.

Another embodiment is a method for generating a stereo image for an object, the method comprising: disposing a translating lens apparatus to receive light from the object, wherein the translating lens apparatus is configured to move a lens laterally to a first extent and laterally to a second extent opposite the first extent, wherein the first extent has a first distance and the second extent has a second distance; moving the lens to the first extent and directing light from the object through the lens to an image capture apparatus; capturing a first image with the image capture apparatus; moving the lens to the second extent and directing light from the object through the lens to the image capture apparatus; capturing a second image with the image capture apparatus; and processing the first image and the second image to produce a stereo image for the object.

Still another embodiment is a system for stereo imaging comprising: a translating lens apparatus, wherein the translating lens apparatus comprises: a translating lens; a lens holder mechanically coupled to the translating lens, wherein the lens holder is configured to move bilaterally; an actuating apparatus mechanically coupled to the lens holder, wherein the actuating apparatus is configured to move the lens holder in a first lateral direction to a first maximum extent and to move the lens holder in a second lateral direction opposite to the first lateral direction to a second maximum extent; and, an imaging apparatus receiving light directed through the translating lens, wherein the imaging apparatus is configured to capture a first image when the lens holder is at the first maximum extent and to capture a second image when the lens holder is at the second maximum extent; a lens controller electrically coupled to the actuating apparatus, wherein the lens controller is configured to control lens movement; a power supply electrically coupled to the lens controller; and, a video processor configured to receive images from the imaging apparatus and further configured to synchronize the lens movement with images received by the video processor and further configured to generate stereo images.

BRIEF DESCRIPTION OF THE SEVERAL VIEWS OF THE DRAWINGS

FIG. 6 shows another system for 3D imaging using a translating lens.

FIG. 7 shows the use of silicon comb actuators for lens movement.

FIGS. 8A-8D illustrate a fabrication process for a lens shuttle and an associated aperture structure.

FIGS. 9A-9D illustrate an alternative fabrication process for a translating lens device.

FIG. 10 shows a photograph of a prototype translating lens device.

FIG. 11 shows a top-down schematic view of the translating lens device shown in FIG. 10.

FIGS. 12A and 12B show photographs of comb drive actuators at two extents.

FIG. 17 shows a miniature sensor based on a fiberscope design to capture 3D images.

FIG. 18 shows a miniature sensor based on the use of a miniature camera.

FIGS. 28A-28D show simulation results for a lens with 400 μm diameter and a 0.5 mm focal length.

FIG. 33 is a front view of the sensor shown in FIG. 17.

FIG. 34 is a front view of the sensor shown in FIG. 18.

FIGS. 36A-36F illustrate the processing used for distance measurement.

DETAILED DESCRIPTION

Instrumentation in modern surgery is evolving to render many procedures available in what is known as MIS and in particular LESS and NOTES which vary depending on the type of surgery. The present invention includes the recognition that for modern surgical procedures there can be improvements with illumination, visualization, and the crossing of instrumentation on the entry point, and insufficient separation between the left hand and the right hand instruments.

The present invention includes the recognition that a possible improvement for endoscopic and laparoscopic procedures is the provision of three-dimensional imaging. This recognition includes the appreciation that one of the most widely used and efficient ways to define an object's appearance is to see it from various angles. Looking from different angles provides valuable 3D information about the object, such as size, distance, and surface profile, which cannot be easily obtained by using images observed only from a single viewpoint.

Given the known limitations with existing stereo-image lens systems, there exists a need in the art for a system that does not require a multiple lens system for stereo-image acquisition. This will reduce overall device size and structural complexity, and especially beneficial in endoscopic and laparoscopic applications where size of the tool is a main concern. There also exists a need in the art for a stereo-image lens system with low manufacturing cost and structural simplicity.

The invention includes embodiments for use of such stereo-imaging apparatus in surgical instrument guides using MEMS technology used for tracking a surgical instrument in the operation field, via contact passive optical range finding to provide information on the relative position between an organ and an approaching instrument tip, so that a surgeon can view more details of the operational fields than through a general observation camera. Embodiments include incorporating such implementations into specified surgical tools used for LESS and NOTES procedures.

Advantages of the subject new embodiments include improvements in illumination, visualization, and the crossing of instrumentation on the entry point, sufficient separation between the left- and right-hand instruments.

Figure 1A:
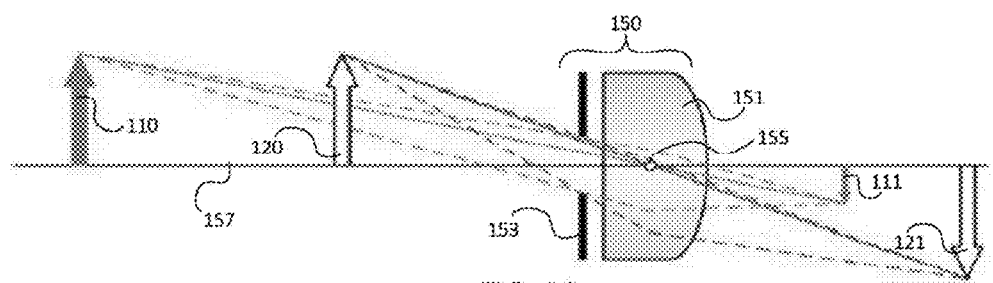
FIGS. 1A-1C illustrate a method for the generation of stereo images.
Figure 1B:
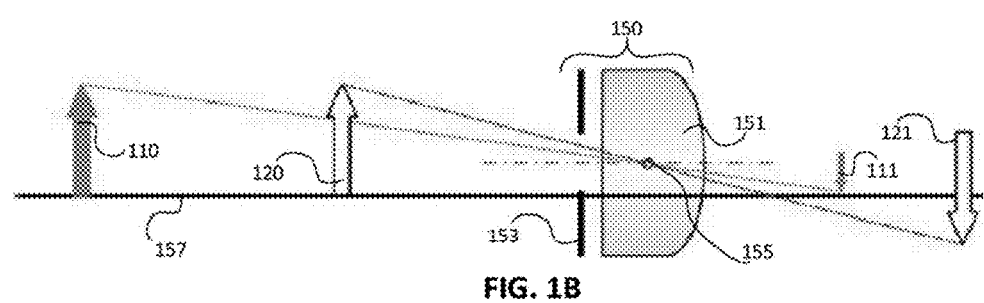
Figure 1C:
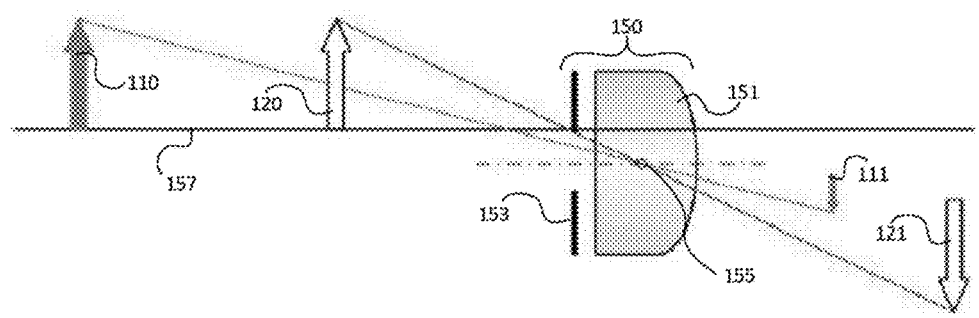

FIGS. 1A-1C illustrate a method for the generation of stereo images. A de-centering of a lens generates image shifts of the objects seen through the lens. In FIGS. 1A-1C, two arrows 110, 120 signify objects standing on an optical axis 157. FIGS. 1A-1C also show a lens structure 150 with a lens 151, lens center 155 and an aperture plate 153. In FIG. 1A, when the lens center 155 is on the optical axis 157, the images 111, 121 of the arrows 110, 120 form behind the lens 151 in an upside down orientation with the images 111, 121 standing under the axis 157. If the lens structure 150 translates upward as shown in FIG. 1B, the arrow images 111, 121 also move up. However, the amount of image shift for each arrow 110, 120 varies based on the physical distance of each arrow 110, 120 from the lens 151. That is, the image of the closer arrow 120 shifts more than that of the farther arrow 110. If the lens structure 150 translates downward as shown in FIG. 1C, the arrow images 111, 121 move down, and the shifting amounts are again based on the distances of the arrows 110, 120 from the lens 151. This relationship between the object distance and the image shift may be used to generate different viewing angles for 3D perception. Comparing the amount of image shift with pre-calibrated data, a system can further estimate how far each object is from the lens.

Figure 2:
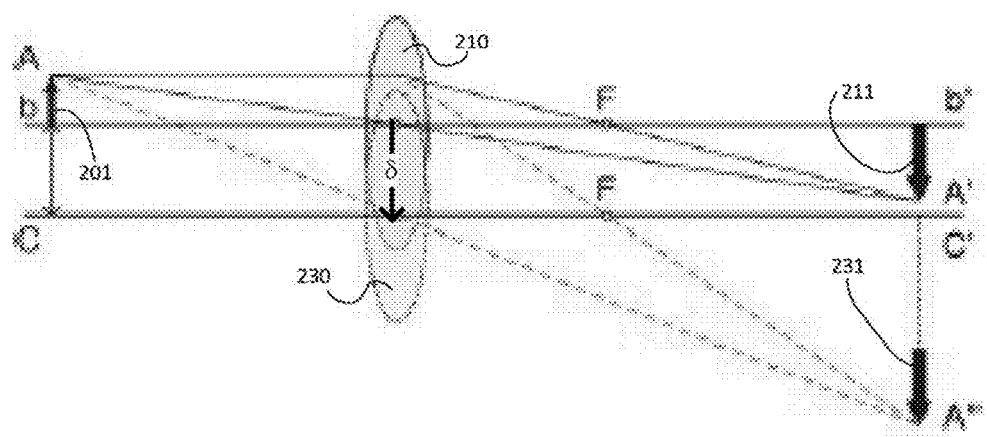
FIG. 2 illustrates the stereo imaging provided by lens translation and shows how the image shift may be estimated.

FIG. 2 further illustrates the stereo imaging provided by lens translation and shows how the image shift may be estimated. In FIG. 2, at the initial position of the lens 210, an object 201 of height $\overline{Ab}$ projects an image 211 of height $\overline{A'b'}$ behind the lens. With a lower located lens 230 shifted by $\delta$ (i.e., the lens translates downwards by $\delta$), the tip of the image moves from A' to A''. If the magnification is $\gamma$, the size of each projected image can be estimated in a paraxial approximation by the following equations (with reference to the points shown in FIG. 2):

$$\overline{A'b'} = \overline{Ab} \times \gamma \quad \text{Eq. 1}$$

$$\overline{A''C} = (\overline{Ab} + \delta) \times \gamma \quad \text{Eq. 2}$$

Then the overall image shift $\Delta$ may be calculated as shown below:

$$\Delta = \overline{A''b'} - \overline{A'b'} = (\overline{A''C} + \delta) - (\overline{Ab} \times \gamma) \quad \text{Eq. 3}$$

$$\Delta = [\{(\overline{Ab} + \delta) \times \gamma\} + \delta] - (\overline{Ab} \times \gamma) \quad \text{Eq. 4}$$

$$\Delta = \delta \times (\gamma + 1) \quad \text{Eq. 5}$$

Figure 3A:
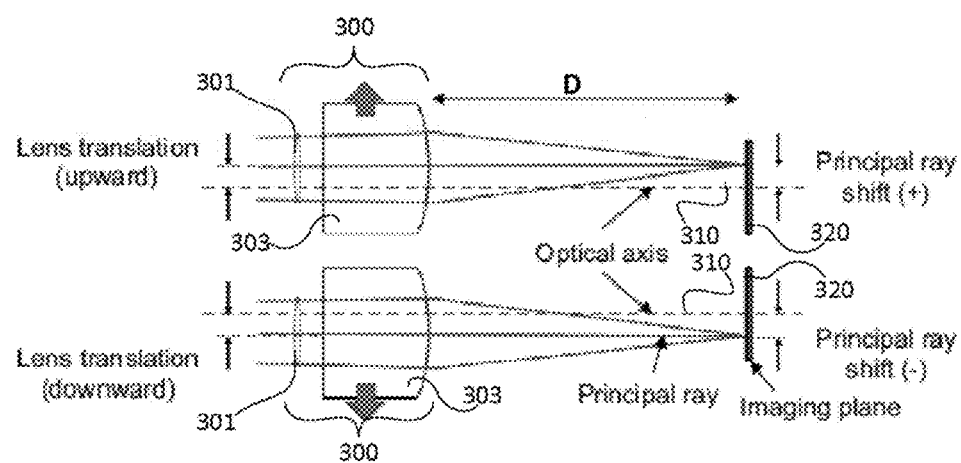
FIG. 3A illustrates the resulting image shift provided by a translating lens.
Figure 3B:
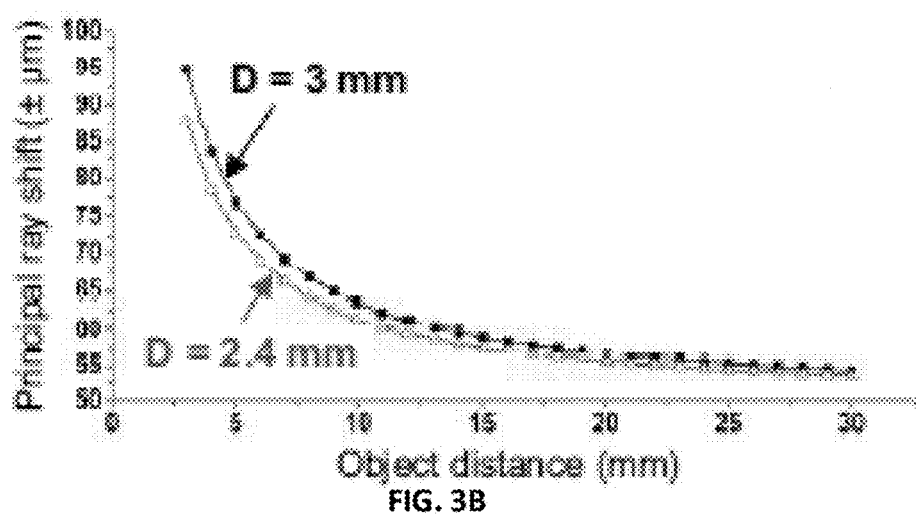
FIG. 3B shows the results for a simulation of the image shifts for varying object distances for two cases.

Eq. 5 shows that the amount of image shift $\Delta$ depends on the lens translating distance $\delta$ and the image magnification $\gamma$, the latter of which is related to the object distance. FIG. 3A further illustrates the resulting image shift provided by a translating lens. In FIG. 3A, a lens unit 300 consisting of a 500 μm diameter aperture 301 located 200 μm from a 2 mm focal length plano-convex lens 303 which translates ±50 μm across the optical axis 310. An imaging plane 320 is located at a distance "D" from the lens 303. FIG. 3B shows the results for a simulation of the image shifts for varying object distances for two cases: the imaging plane 320 located 2.4 mm or 3 mm behind the lens (focusing point: 10 mm or 5 mm in front of the lens, respectively). The result verifies that the principal ray shifts more if the object is closer to the lens or the imaging plane is farther from the lens (i.e., the gap "D" in FIG. 3A is larger). This optical simulation was run for object distances in the range of 3-30 mm, which is practical for endoscopic applications. Table 1 below shows calculated principal ray shifts versus object distance for lens translations of ±50 μm, ±75 μm, and ±100 μm.

TABLE 1

| | Principal ray shift (± μm) Δ | | |
|---|---|---|---|
| Object distance (mm) | ±50 μm aperture and lens translation (δ) | ±75 μm aperture and lens translation (δ) | ±100 μm aperture and lens translation (δ) |
| 3 | 94.9 | 142.3 | 189.8 |
| 4 | 83.7 | 125.5 | 167.3 |
| 5 | 76.9 | 115.4 | 153.9 |
| 6 | 72.5 | 108.7 | 144.9 |
| 7 | 69.2 | 103.9 | 138.5 |
| 8 | 66.8 | 100.2 | 133.7 |
| 9 | 65.0 | 97.5 | 130.0 |
| 10 | 63.5 | 95.2 | 126.9 |
| 11 | 62.2 | 93.4 | 124.5 |
| 12 | 61.2 | 91.8 | 122.5 |
| 13 | 60.4 | 90.5 | 120.7 |
| 14 | 59.6 | 89.4 | 119.2 |
| 15 | 59.0 | 88.5 | 118.0 |
| 16 | 58.4 | 87.6 | 116.8 |
| 17 | 57.9 | 86.9 | 115.8 |
| 18 | 57.5 | 86.2 | 115.0 |
| 19 | 57.1 | 85.6 | 114.1 |
| 20 | 56.7 | 85.1 | 113.5 |

TABLE 1-continued

| | Principal ray shift (± μm) Δ | | |
|---|---|---|---|
| Object distance (mm) | ±50 μm aperture and lens translation (δ) | ±75 μm aperture and lens translation (δ) | ±100 μm aperture and lens translation (δ) |
| 21 | 56.4 | 84.6 | 112.8 |
| 22 | 56.1 | 84.2 | 112.2 |
| 23 | 55.9 | 83.8 | 111.7 |
| 24 | 55.6 | 83.4 | 111.2 |
| 25 | 55.4 | 83.1 | 110.8 |

Figure 4:
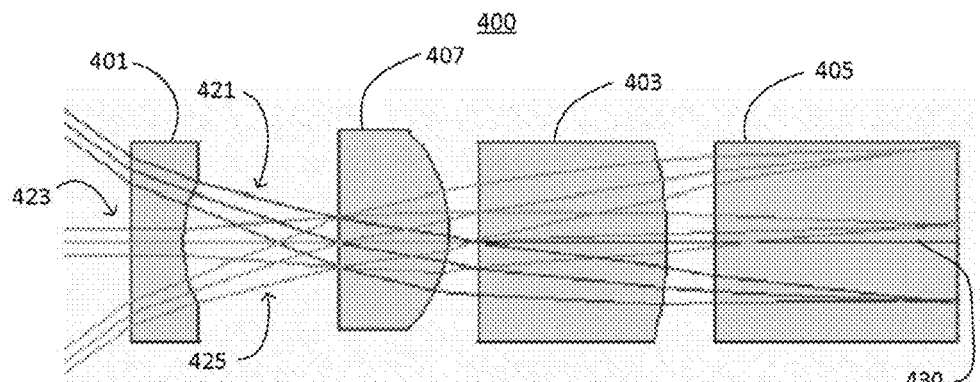
FIG. 4 shows an objective lens group consisting of three fixed lenses, and a translating (i.e., a bilaterally movable) lens.

Relative image shifts depending on the object distances as described herein enables 3D viewing by providing different viewing angles to the observer, and the calibrated image shift tables can be used to measure distance to an object. This method not only works by translating a single lens in front of the sensor, but also by translating one of an objective lens group. FIG. 4 shows an objective lens group 400 consisting of three fixed lenses 401, 403, 405, and a translating (i.e., a bilaterally movable) lens 407. Simulated ray traces 421, 423, 425 show the path of light rays through the various lenses 401, 403, 405, 407, with the translating lens 407 shifted slightly upward such that the rays 421, 423, 425 and shifted in an upward direction from the optical axis 430.

Figure 5:
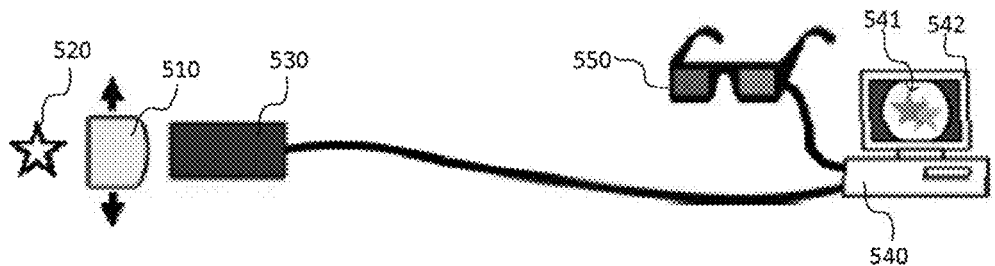
FIG. 5 shows a system for 3D imaging using a translating lens.

One system for 3D imaging using a translating lens is shown in FIG. 5. In FIG. 5, a translating lens 510 directs light from an object 520 to a camera 530. The camera 530 may be a charge-coupled device (CCD) camera to provide small size and weight. The camera 530 sends its signals to a processing system 540, which processes the signals and generates images 541 on a display 542. The images 541 may then be viewed through an appropriate 3D viewing apparatus 550, such as passive or active 3D glasses. The processing system 540 uses information regarding the translation of the lens 510 to provide the appropriate dimensional offset between images 541 on the display 542 to provide the 3D effect.

A system that provides for a more compact system is shown in FIG. 6. Such a system may find use in applications such as endoscopy. FIG. 6 shows a stereo imaging system consisting of an imaging fiber bundle 610, a translating lens system 620, a transducer lens 625 and a camera 630 (e.g., a CCD camera) connected to a control computer 640. The translating lens system 620 contains a lens unit (not shown in FIG. 6) packaged in the lens system 620 that is positioned in front of the fiber bundle 610. The images of an object 605 are directed into the fiber bundle 610 through the translating lens system 620. The transducer lens 625 directs images from the fiber bundle 610 to the camera 630. As discussed above, the control computer 640 processes the images from the camera 630 and lens translation information to provide images 641 that are sent to the display 642 for viewing by a 3D viewing apparatus 650. The control computer 640 synchronizes the camera 630 with an electrical signal that drives the lateral translation of the lens unit in the translating lens system 620. The images captured by the synchronized camera 630 in real-time are used for 3D viewing or object distance measurement.

The translating lens system 620 in FIG. 6 may be provided by silicon comb drive actuators as shown in FIG. 7. In FIG. 7, a lens unit 710 is embedded in a lens shuttle 720. The lens shuttle 720 has two sets of silicon comb drive actuators 722 that provide for bilateral motion. The lens shuttle 720 is suspended by two folded spring fixtures (not shown in FIG. 7) that facilitate the lateral translation. FIGS. 8A-8D illustrate a fabrication process for the lens shuttle 720 and an associated aperture structure 750. FIG. 8A shows an Silicon-on-Insulator (SOI) wafer with a 50 μm-thick Si device layer 810, a 0.5 μm-thick buried oxide layer 820, and a 350 μm-thick Si handle layer 830. To eliminate additional electrode deposition and patterning, a heavily doped Si device layer of the SOI is chosen for creating the electrodes of the electrostatic comb actuators. First, the bottom handle layer 830 of the SOI wafer is anisotropically etched by deep reactive ion etching (DRIE), followed by removal of the exposed buried oxide layer 820 by reactive ion etching (RIE) as shown in FIG. 8B. The device layer 810 of the SOI is then patterned by DRIE to form the comb drive actuators 858 on the shuttle device and to make a hole 871 that is 500 μm in diameter on the aperture structure 750, as shown in FIG. 8C. The aperture structure 750 is released at the same time in this step. A plano-convex lens 860, (such as the NT65-253, Edmund Optics, NJ, USA) 1 mm in diameter and 800 μm in thickness, is inserted into the fabricated aperture structure 750 with a 150 μm-thick ring spacer 864 in between to ensure the proper gap between the lens 860 and the aperture screen 862. The lens 860 has an effective focal length of 2 mm, as discussed in the optical simulation described above. As the last step, the assembled aperture structure 750 with the lens 860 is inserted in the silicon shuttle 720, as shown FIG. 8D. The device is 10 mm×10 mm in overall dimension.

An alternative process for fabricating a translating lens device is shown in FIGS. 9A-9D when no silicon aperture structure needs to be fabricated (i.e., a lens is already equipped with an aperture). In FIG. 9A, an SOI wafer with a heavily doped Si device layer 910, a buried oxide layer 920, and a Si handle layer 930 is used as starting material. FIG. 9B shows the bottom Si handle layer 930 anisotropically etched by DRIE to form a trench 932 and to remove the exposed portions of the buried oxide layer 920. FIG. 9C shows the top Si device layer 910 etched to form comb drive actuators 912 and to create an opening 914 for a lens. FIG. 9D shows that after the remaining oxide on the top layer was removed, a lens unit 916 was inserted into the opening in the device layer 910. The lens unit 916 may be held in place by a silicon ring 918.

Figure 32:
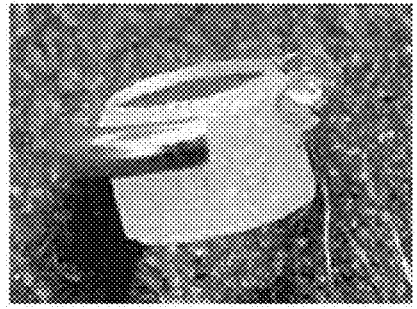
FIG. 32 is a photograph of a COTS lens.
Figure 37:
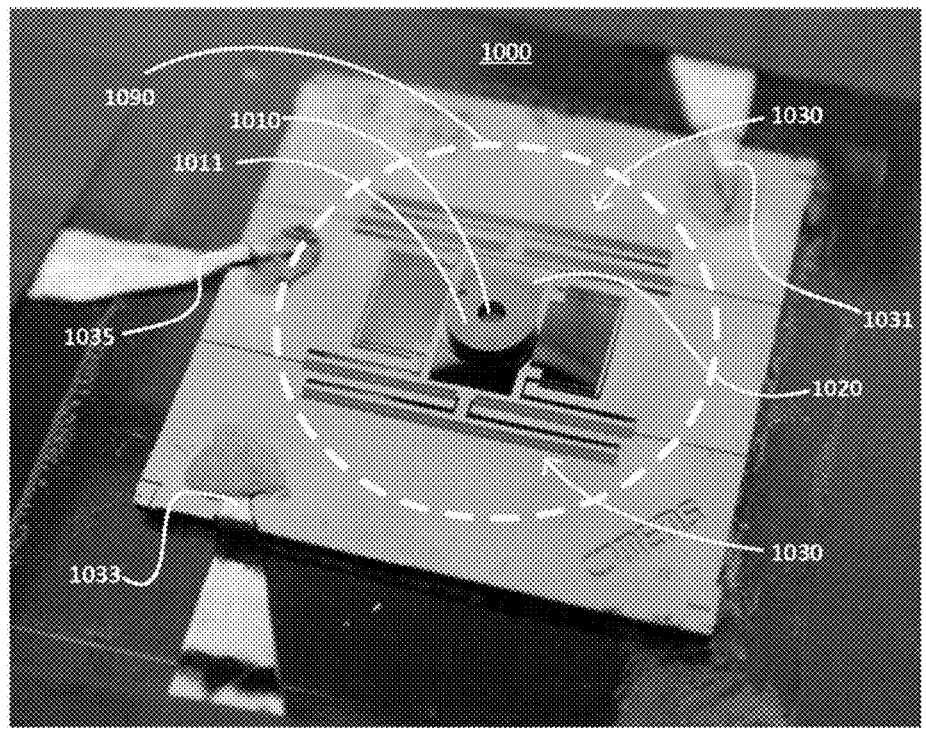
FIG. 37 shows a photograph of a prototype translating lens device with a silicon aperture structure disposed above the lens.

FIG. 10 shows a photograph of a prototype translating lens device 1000 using a 1 mm diameter Commercial Off-the-Shelf (COTS) lens 1010 (Part # NT65-253 from Edmund Scientific). FIG. 32 is a photograph of the COTS lens 1010. FIG. 37 shows the translating lens device with a silicon aperture structure 1011 disposed above the lens 1010. The device 1000 shown in FIG. 10 may be fabricated according to the processes described above, or using other semiconductor or Micro-Electro-Mechanical System (MEMS) fabrication techniques known in the art. The device 1000 shown in FIG. 10 is fabricated on a 10×10 mm silicon slab. Other devices may be created by removing excess silicon (represented by the dotted circle 1090) to result in a smaller diameter device, e.g., a 3.5 mm diameter device. In FIG. 10, the lens unit 1010 is held in a lens holder 1020. The lens holder 1020 is mechanically coupled to comb drive actuators 1030. Lens motion is achieved when a voltage is applied between an electrode 1031, 1033 and a ground contact 1035. In the configuration depicted in FIG. 10, a total translation distance of 100 μm (±50 μm) was achieved with the application of 24V. Greater translation distances may be achieved with higher voltages, e.g., 44 VDC or greater. Experimental results showed that a shift of 100 μm in this configuration did not affect the image quality provided by the lens 1010.

Figure 38:
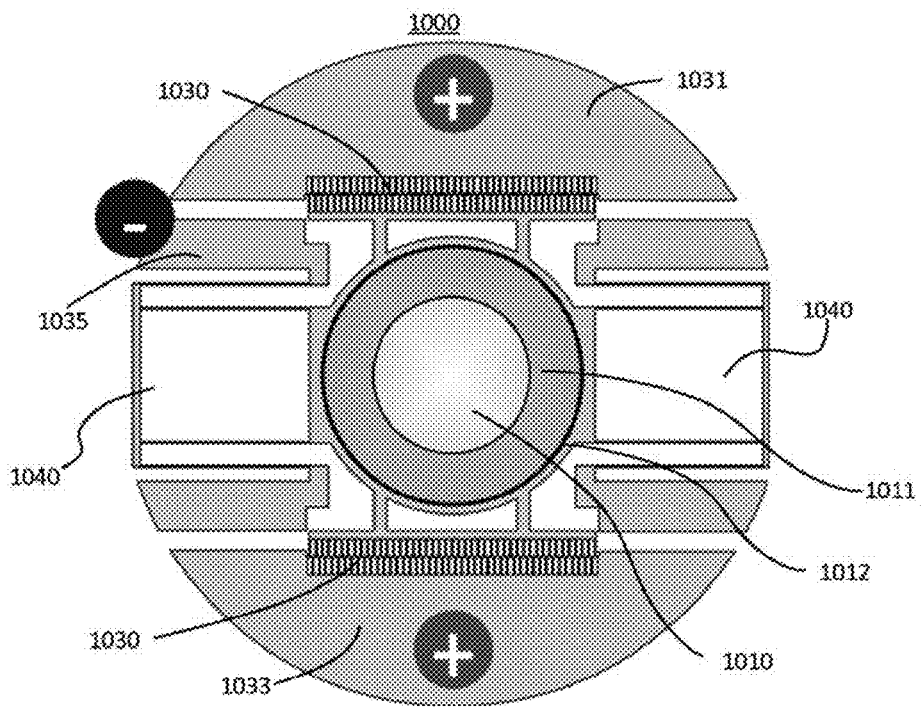
FIG. 38 shows a top-down schematic view of the translating lens device shown in FIG. 37.

FIG. 11 shows a top-down schematic view of the translating lens device 1000 shown in FIG. 10. The device 1000 has the lens 1010 placed on a silicon ring 1012. The silicon ring 1012 is suspended by two 1 mm long and 6 μm wide silicon folded microbeams 1040, which act as springs. Two sets of comb drive actuators 1030, each of which has 700 moving fingers, provide the drive to linearly translate the lens 1010 towards an upper electrode 1031 or towards a lower electrode 1033. In operation, voltage is applied between the upper electrode 1031 or lower electrode 1033 and a ground electrode 1035. FIG. 38 shows the lens 1010 with an aperture structure 1011 that contains an aperture (i.e., a hole) with smaller diameter than that of the lens 1010 that serves to collimate the light rays directed through the lens 1010. The aperture is disposed between the lens 1010 and the area from which light rays are received. The aperture structure 1011 may be attached directed to the lens 1010 or otherwise configured to move with the lens. A lens having a 1 mm diameter and a 0.5 mm focal length may have an aperture of 0.5 mm. FIGS. 12A and 12B illustrate the structure of the comb drive actuators. FIGS. 12A and 12B show interdigitated fingers 1037, 1038 that are 120 μm in length, 5 μm in width and 50 μm thick. The gap 1039 between the fingers 1037, 1038 is 3 μm. FIG. 12A depicts the state where the actuator is not energized such that the movable fingers 1038 of the comb drive actuator overlap with the fixed fingers 1039 by about 10 μm within the gap 1039. FIG. 12B depicts the state where the actuator is energized such that the movable fingers 1038 are drawn into the gaps 1039 between the fixed fingers 1037 providing movement up to 50 μm or greater with the application of 24 VDC or greater.

An alternative design, similar to that shown in FIG. 11, may use single-folded beams with shorter springs. To maintain a similar spring constant with a shorter spring, the beam width will need to be reduced. In this design, silicon rim segments outside of the moving structure would be eliminated. That may require a modification in the release procedure of the flextures and combs to prevent "stiction" during fabrication. However, such a design may allow the use of a larger lens.

Figure 13:
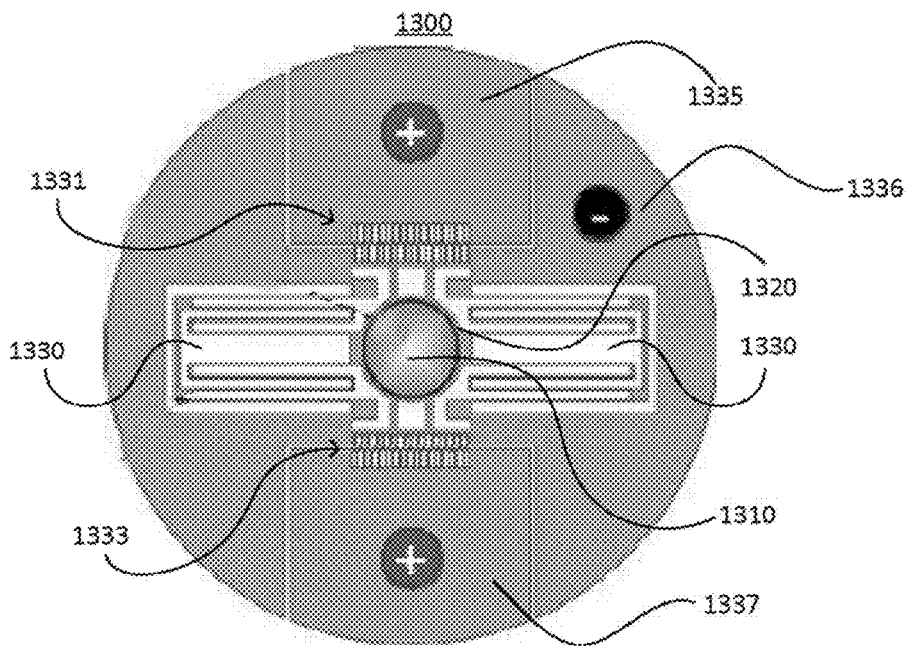
FIG. 13 shows a top-down view of a reduced size translation lens device utilizing a triple-folded beam spring structure.

FIG. 13 shows a top-down view of a reduced size translation lens device 1300 utilizing a triple-folded beam spring structure 1330 to facilitate lens motion. The device 1300 shown in FIG. 13 may have a diameter of 2.5 mm or less and may be fabricated using existing semiconductor or Micro-Electro-Mechanical System (MEMS) fabrication techniques. Some of the size reduction can be achieved by eliminating portions of peripheral structure areas (see, for example, areas outside the circle 1090 shown in FIG. 10). In FIG. 13, a lens 1310 is held by a lens holding structure 1320. The lens 1310 may have a diameter from 300 μm to 400 μm with focal lengths from 0.3 mm to 1.0 mm, or other diameters and focal lengths according to desired size and functionality. For example, devices in accordance with the teachings herein may have lenses ranging from 50 μm to 2000 μm. In some embodiments, but not shown in FIG. 13, the lens 1310 has an aperture plate disposed between the lens and the area under observation. The aperture plate contains an aperture that collimates light rays directed through the lens 1310. The aperture plate may be integrated with the lens or may be a separate structure. Note, however, that the aperture within the aperture plate translates with the lens. The lens holding structure 1320 is mechanically coupled to comb drive actuation areas 1331, 1333. Each of the triple-folded beam structures 1330 may have a beam that is 6 μm wide and consist of four 500 μm long members. The triple-folded beam structures 1330 sustain the weight of the lens 1310. Note that a lens with a diameter from 300 to 400 µm will have a reduced weight, which will allow the overall size of the structure to be reduced and may also allow for a larger lens translation due to a lower weight of the lens 1310. Comb electrodes 1335, 1337 are used to provide voltage to fixed segments of the comb drive actuation areas 1331, 1333 and the movable segments of the comb drive actuations areas 1331, 1333 are electrically coupled to a ground electrode 1336. When a heavily doped silicon device layer is used to fabricate portions of the electrodes 1335, 1336, 1337, metal wires may be directly connected to the silicon electrode surfaces with silver paint, making boding or soldering unnecessary.

Figure 28C:
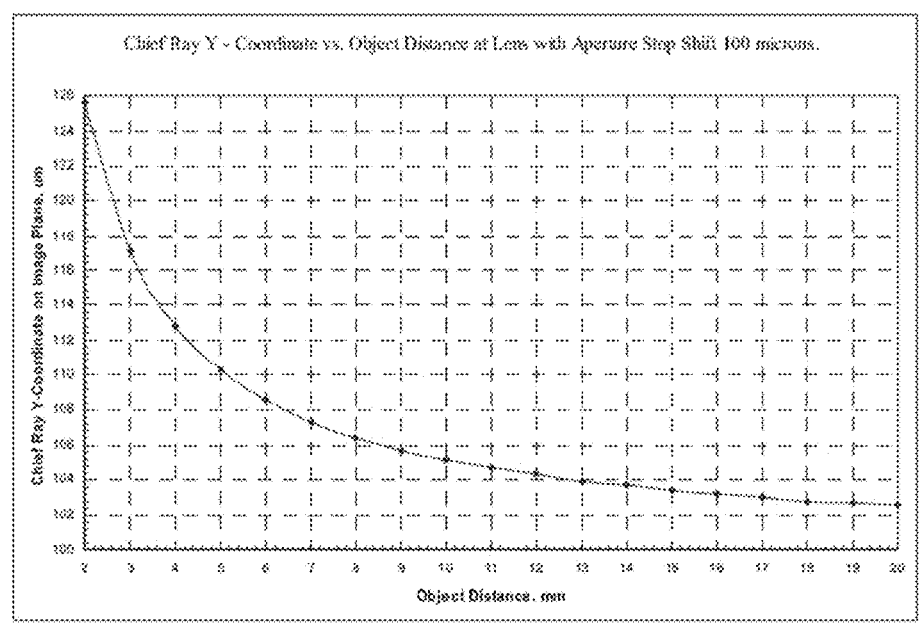
Figure 28A:
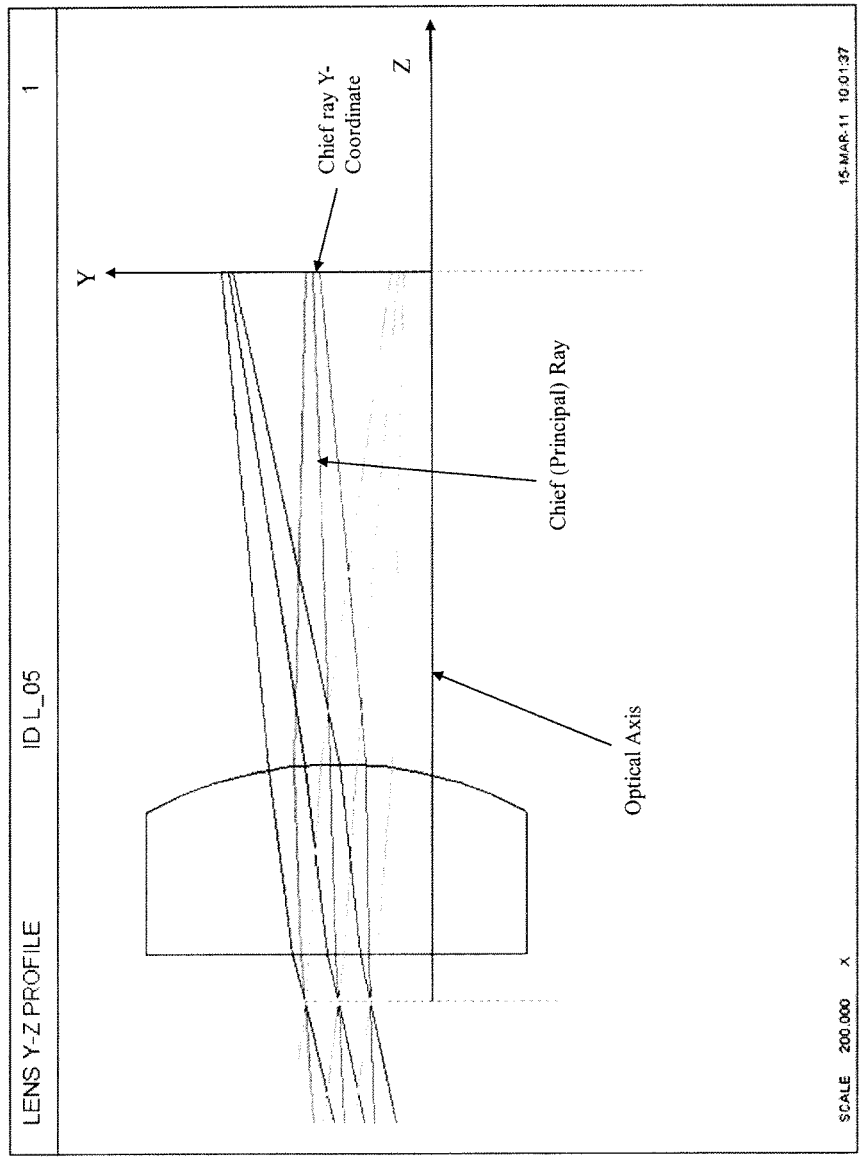
Figure 28B:
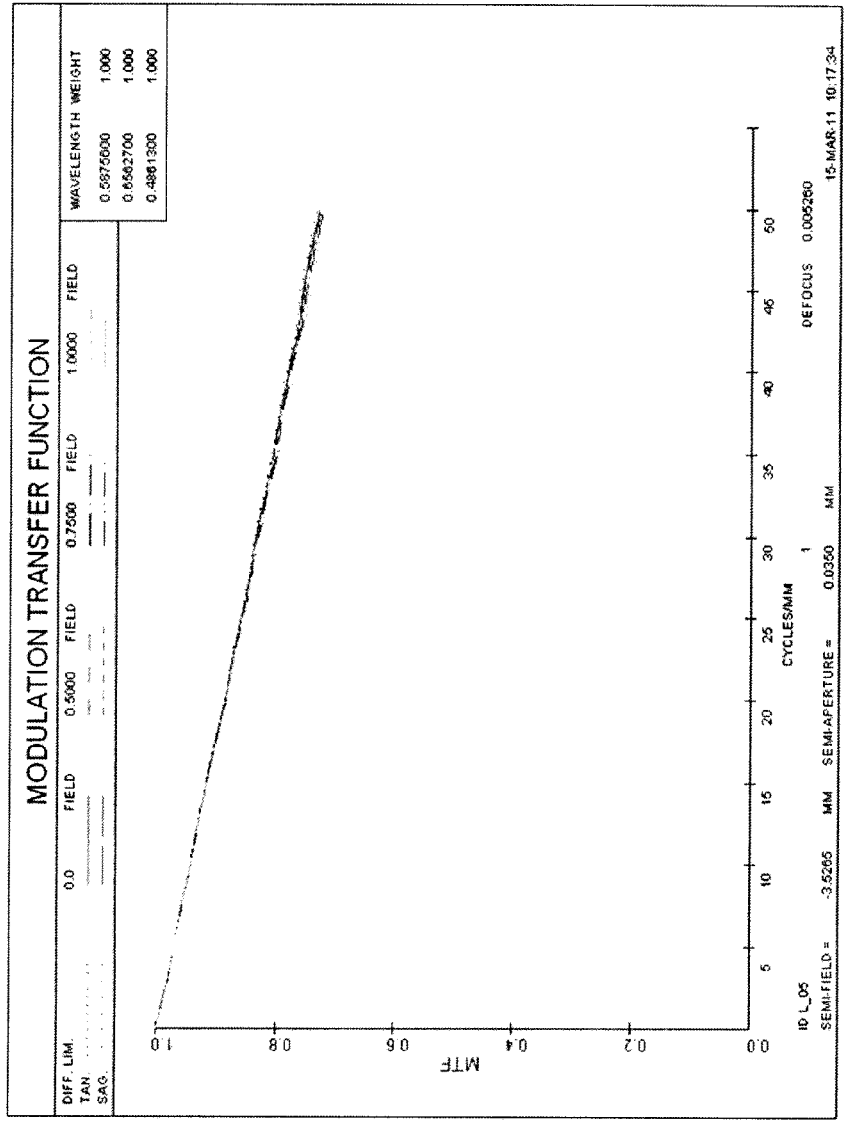
Figure 29A:
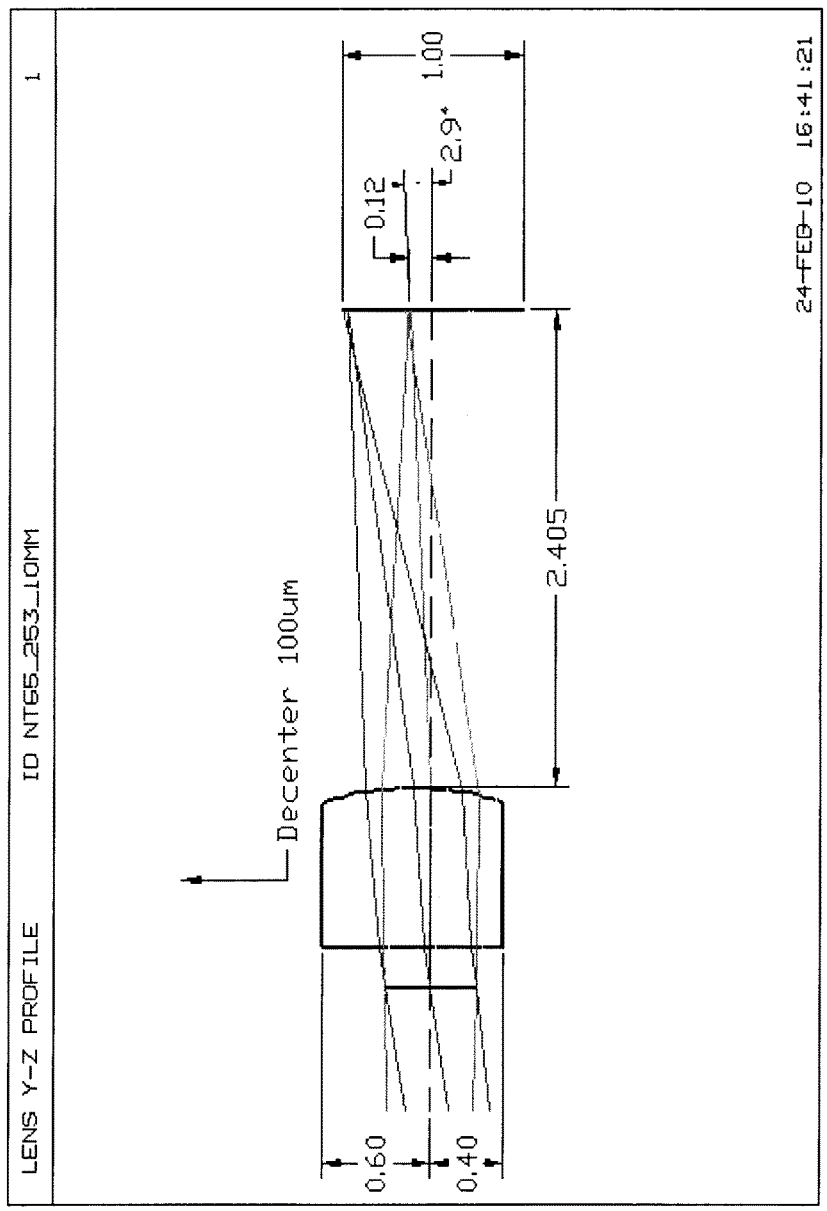
FIGS. 29A-29C show simulation results for a 1 mm diameter lens.
Figure 29B:
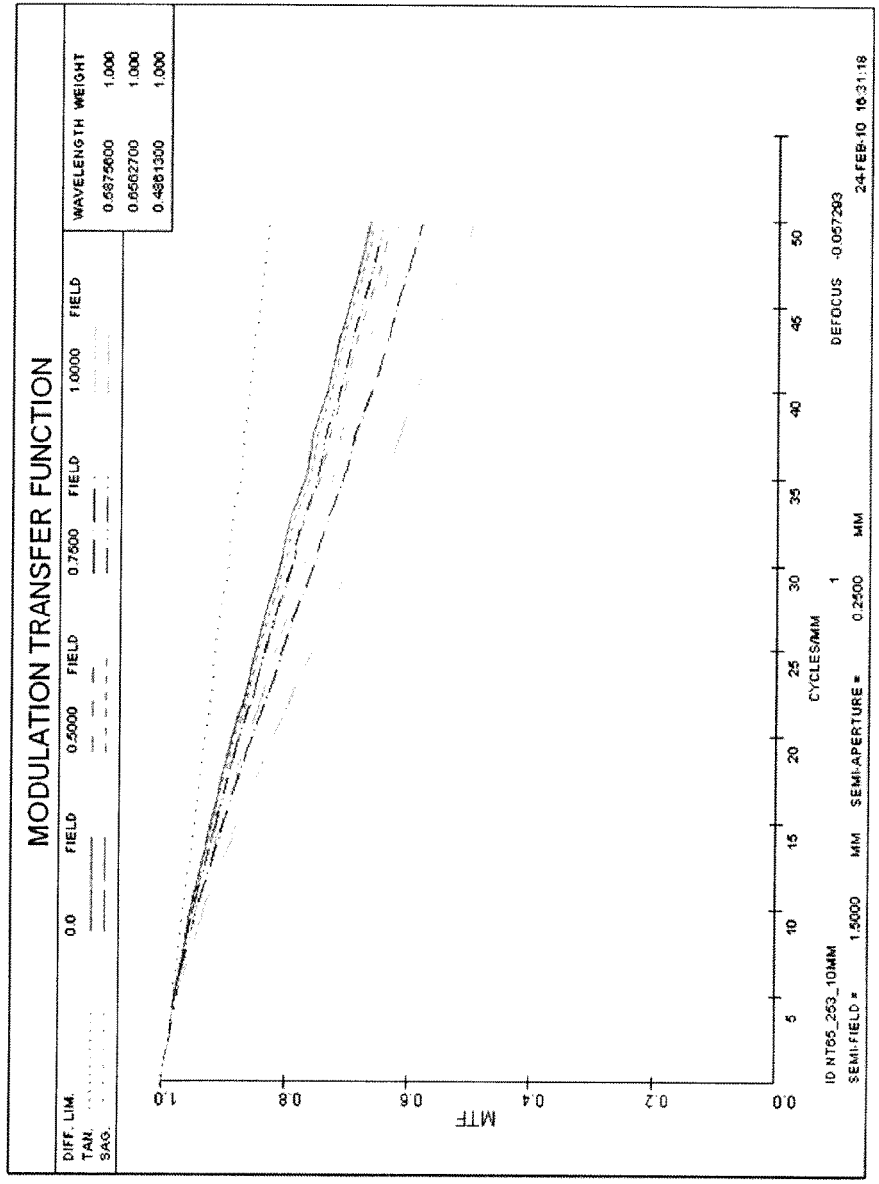
Figure 29C:
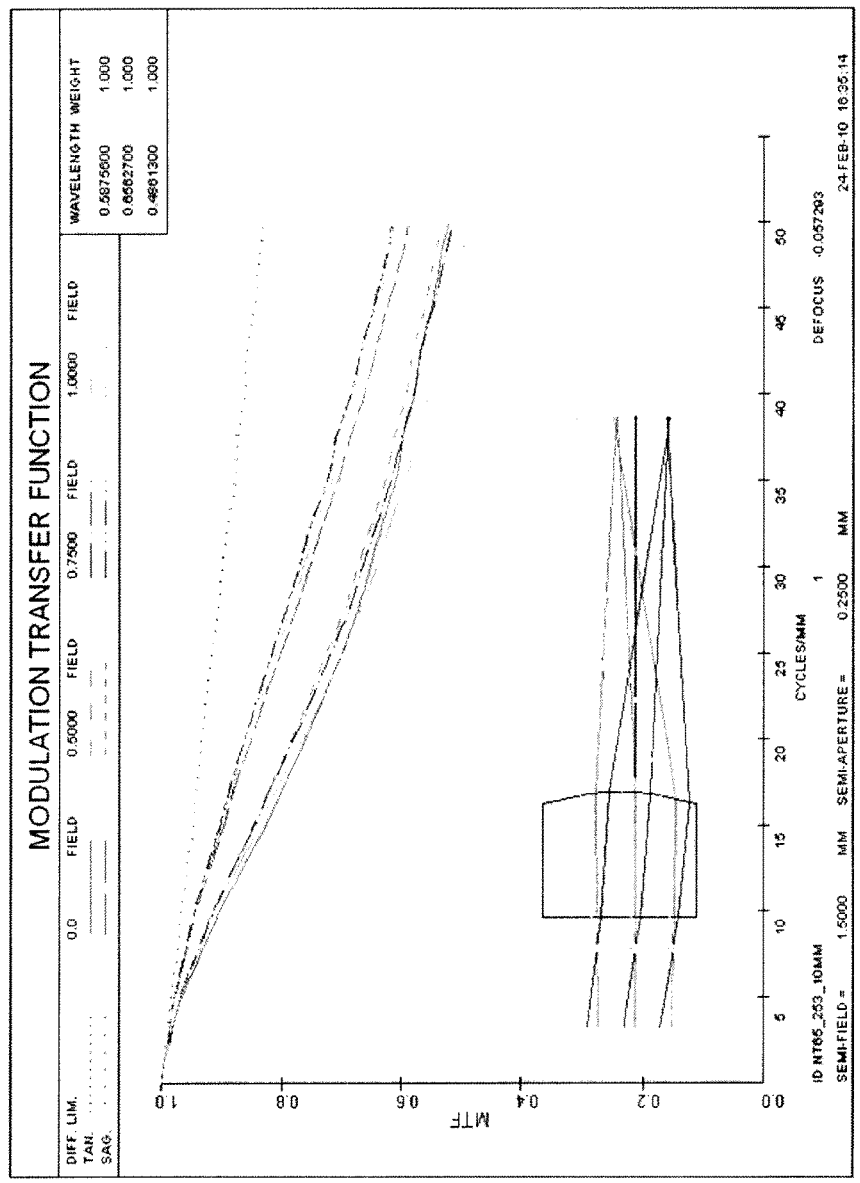

Lens design in the translating lens devices described herein may be particularly important to obtain high quality images and to avoid suffering image degradation when the lens is shifted. As noted above in regard to device 1300 shown in FIG. 13, the lens 131 may have a diameter from 300 to 400 µm. Simulations show that a properly designed lens with a 400 µm diameter and a 0.5 mm focal length should provide sufficient quality images with a lens shift of up to 100 µm. The results of these simulations are shown in FIGS. 28A-28D. FIG. 28A shows the ray tracing for such a lens at a 100 µm shift. FIG. 28B shows the modulation transfer function of the shifted lens at the distance to the object of 20 mm. FIG. 28C shows a plot of the shift versus distance. FIG. 28D shows a table of the data plotted in FIG. 28C. As discussed above. The translating lens device 1000 shown in FIG. 10 uses a 1 mm diameter lens. Simulations were also run for this lens and the results of the simulations are shown in FIGS. 29A-29C. FIG. 29A shows a graphical representation of the ray tracing results with a 100 µm shift with an object at a distance of 10 mm. FIG. 29B shows the modulation transfer function for a non-shifted lens with an object distance of 10 mm. FIG. 29C shows the modulation transfer function for a lens shifted by 100 µm with an object distance of 10 mm.

Figure 14A:
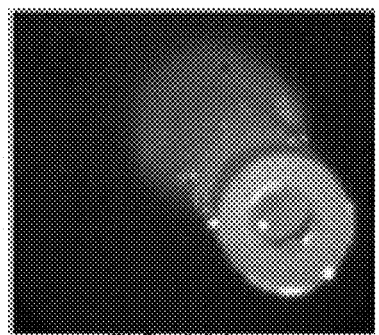
FIGS. 14A-14D show the results of a stereo image test used to image a plastic pipette tip.
Figure 14B:
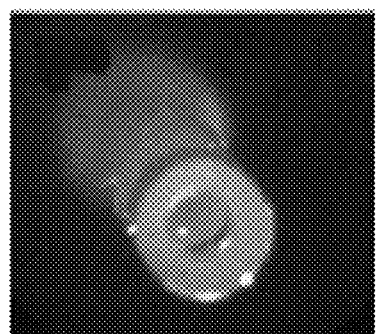
Figure 14C:
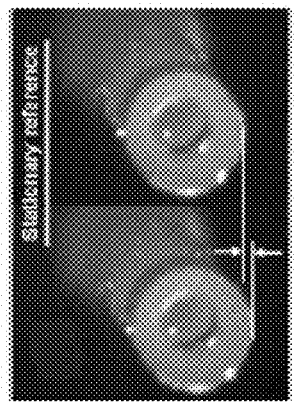
Figure 14D:
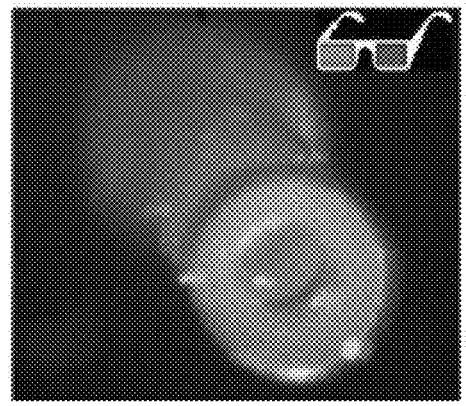

The prototype translating lens device 1000 shown in FIG. 10 was used to image a plastic pipette tip approximately 3 cm long as a target object for a stereo image test. FIGS. 14A-14D show the results of that stereo image test. FIG. 14A shows the image obtained with the lens translated to one 50 µm extent. FIG. 14B shows the image obtained with the lens translated to the opposite 50 µm extent (i.e., the lens was translated ±50 µm). Note that the entire image of the target translates more than ±50 µm, but the image of the closer part (the tip of the pipette tip) moves more than that of the faraway part (the base of the pipette tip) as predicted by the simulations discussed above when the lens is focused for 5 mm length. In FIG. 14C, the two captured images have been aligned to a stationary reference point so that only their relative shift can be seen. Two points—one each in FIG. 14A and FIG. 14B, that represent an identical spot on the pipette tip's base are used as the common reference point. As a result, the two images in FIG. 14C have a disparity near the target's tip area while the base area is kept unmoved, i.e., the object appears tilted between the two images. Using superimposed and color-converted images from FIG. 14C, FIG. 14D presents the anaglyph stereo image, providing 3D perception of the target object when viewed in color to a viewer wearing red/cyan anaglyphic glasses (i.e., the pipette tip appears to be protruding out of the display).

Figure 15A:
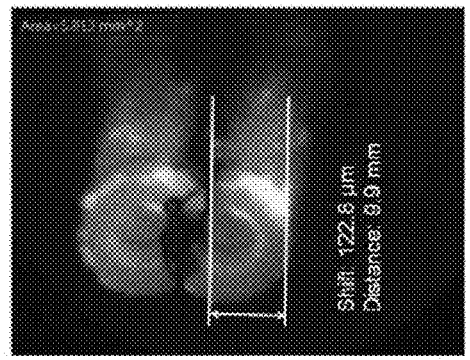
FIGS. 15A and 15B shows the object distance measurement by an endoscopic lens translation system using the same pipette tip as shown in FIGS. 14A-14D.
Figure 15B:
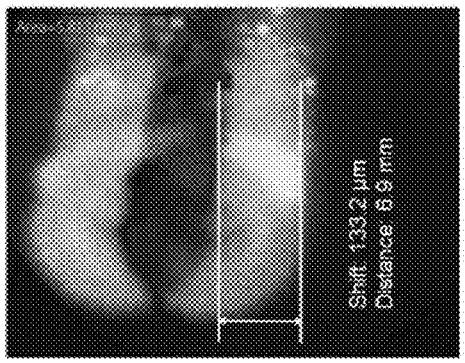

FIGS. 15A and 15B shows the object distance measurement by the endoscopic lens translation system using the same pipette tip as shown in FIGS. 14A-14D. The object tip is 10 mm away from the device and is focused upon by the lens. Therefore, the gap between the lens and the imaging fiber is 2.4 mm ("D" in FIG. 3A), and the image shift vs. distance follows the lower curve in the graph in FIG. 3B. A LabVIEW-based shift-detecting program detects the shifts at the edge area and converts them into a distance. FIGS. 15A and 15B show two captured images added together to find shifted edges. A contrast difference allows the detection of the image shift. In FIG. 15A, the object is 10 mm away from the imaging device and a shift of 122.8 µm is detected. In FIG. 15B, the object is 7 mm away from the imaging device and a shift of 133.2 µm is detected. Using the lower curve in the graph in FIG. 3B, these image shifts correspond to object distances of 9.9 mm and 6.9 mm, respectively. As shown in FIGS. 15A and 15B, use of the translating lens device successfully measured the distance to the object as it was moved closer to the lens device.

One application of the translating lens device for stereo imaging is to support endoscopic and laparoscopic surgical procedures. The small size of the translating lens device adapts well for use with surgical tools used for such surgical procedures. The translating lens device may be incorporated into a miniature sensor for use in minimally invasive surgical procedures such as laparoendoscopic single-site surgery (LESS) and natural orifice transluminal endoscopic surgery (NOTES). Such a sensor may be used for tracking a surgical instrument in the operation field, via noncontact passive optical range finding, and may provide information on the relative position between an organ and an approaching instrument tip, so that the surgeon can view more details of the operational field than typically provided through a general observation camera.

NOTES and LESS surgical procedures have been developed in an attempt to further reduce the morbidity and scarring associated with surgical intervention. Conceptually, these techniques share a common underlying "hypothesis" that has driven their development namely, that a reduction in the number of transcutaneous points of access may benefit patients in terms of port-related complications, recovery time, pain, and cosmesis by potentially performing scarless surgery. NOTES involves diagnostic or therapeutic interventions performed via existing orifices of the human body (mouth, anus, urethra, vagina). Technical challenges associated with NOTES have led to an increasing interest in single-incision or single-port laparoscopy typically referred to as LESS. Urologists have achieved great success in performing LESS procedures. They have successfully performed various procedures with LESS, including partial nephrectomy, pyeloplasty, orchiectomy, orchiopexy, ureterolithotomy, sacrocolpopexy, renal biopsy, renal cryotherapy, and adrenalectomy. To date the estimated cumulative clinical experience worldwide in LESS urology is of more than 500 cases, while NOTES is generally considered to still be in the experimental stage.

LESS access can be obtained either by performing a single-skin and facial incision, through which a single multichannel access platform is placed (single-port surgery), or by placing several low-profile ports through separate facial close incisions (single-site surgery). The close proximity of the instrument and camera insertion ports introduces major obstacles such as potential collisions between instruments and the laparoscope camera, requiring significant coordination between the surgeon and the camera operator; the parallel and close positioning of the right- and left-hand instrument shafts tends to result in crowding of the laparoscope and instruments. Dissection through a single port is also more difficult than in conventional multiport laparoscopy because of the lack of instrument triangulation, and the single laparoscopic camera with a fixed direction of view cannot provide the necessary visualization in the constrained and crowded operating environment. The traditional laparoscopic tools cannot resolve these problems, and a number of novel ones with more advanced features than those of traditional laparoscopic equipment have been developed, but the problems are not solved yet, and the tools are under constant development and improvement. Substantial experience and in many cases the intuitive movement of the surgeon are required to navigate the instruments.

A system using a translating lens device as described herein may be helpful in solving many problems in LESS and NOTES surgeries in the future. The translating lens device may be packaged as a miniature endoscopic probe, but because of the unique optomechanical MEMS at its tip, the device delivers a 3D image and acts as a rangefinder that becomes more accurate as the distance to the object decreases. Whether detached or incorporated in the surgical tool, a system incorporating the translating lens device can be configured to provide the following capabilities: (1) Trace the instrument movement after insertion by visualization. This will enable the surgeon to better control the instrument; (2) Warn the surgeon that the instrument is near tissue or another instrument through non-contact measurement of the distance to the object. This will reduce tissue damage and allow better instrument placement; and (3) Display a 3D image of the local area independent of the host laparoscopic camera. This image can be supplemental to that of the host camera, or even substitute for it when the host camera is obstructed. Further, the role of robotic surgery is rapidly growing in urology and it is expected that robotics will progressively replace standard laparoscopy. Robotic instruments dedicated to LESS and NOTES have recently been introduced by the da Vinci robotic surgical system, and are now under evaluation. The new robotic systems enhance range of motion through use of 'wristed' instrumentation, in addition to improved dexterity and precision with motion scaling and tremor control. Systems incorporating translating lens devices may also be used with robotic surgery systems due to the improved three-dimensional imaging and range finding capabilities provided by such devices.

Figure 16:
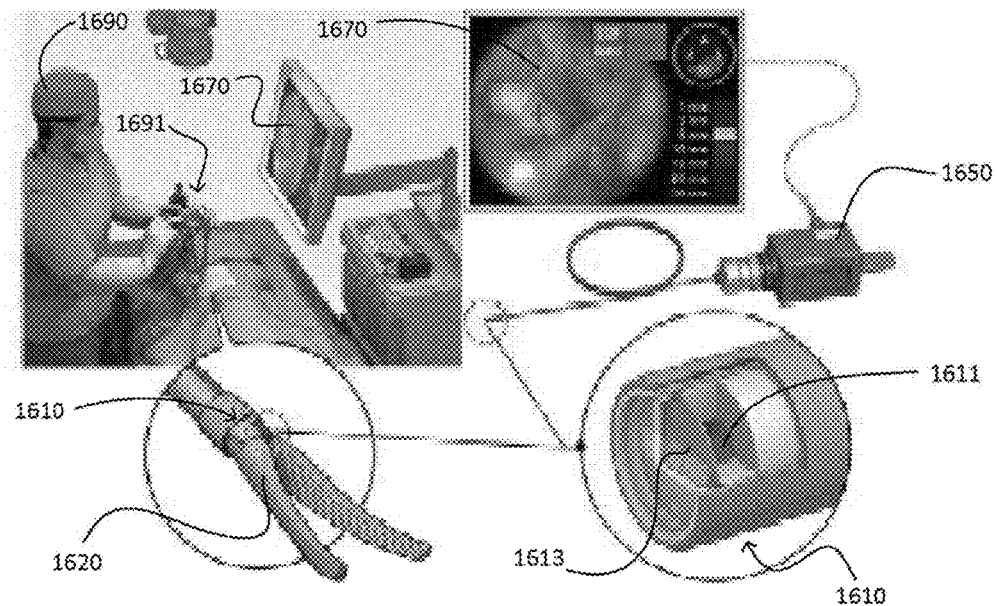
FIG. 16 shows the use of a translating lens device in a surgical environment.

FIG. 16 shows the use of a translating lens device in a surgical environment. A tip of a miniature sensor 1610 containing a translating lens is attached to a surgical instrument such as a grabber 1620. The miniature sensor 1610 comprises a miniature camera 1611 with a translating lens device 1613 in front of it. The miniature sensor 1610 is electrically and/or optically connected to a hardware and firmware box 1650 that conditions signals for image processing and controls the electronics within the miniature sensor 1610. Image processing provides a 3D image 1670 which also contains information about the distance to the displayed tissue. A surgeon 1690 is then able to view this 3D image to assist in controlling the instruments 1691 used for surgery.

FIG. 17 shows a miniature sensor 1700 based on a fiberscope design to capture 3D images. FIG. 33 is a front view of the sensor 1700. As shown in FIG. 17, an imaging fiber or fiber bundle 1720 is positioned behind a MEMS-based translating lens device 1730 (i.e., a MEMS plate). The imaging fiber or fiber bundle 1720 may be surrounded by a fiber ferrule 1723 and/or an intermediate tube 1727. The translating lens device 1730 has a translating lens 1731 that directs light towards the imaging fiber 1720. A window 1740 is used to seal the front end of the sensor 1700. Electrical energy to control the translating lens device 1730 is carried to the device 1730 by wires 1735. The sensor may also contain additional optical fibers 1770 that provide illumination to the area being imaged. An outer sleeve 1710 surrounds all of the interior components to protect those components from damage. As discussed above in regard to FIG. 6, images are directed through the fiber bundle 1720 back to a camera for processing and display. In this configuration, the lens device 1730 may have a diameter of 3.5 mm or less resulting in a device 1700 having a diameter of 4.5 mm or less. Other devices configured as shown in FIG. 17 may have components (e.g., lens device 1730, fiber bundle 1720, etc.) that are sized to result in the devices having diameters larger than 4.5 mm.

Figure 19A:
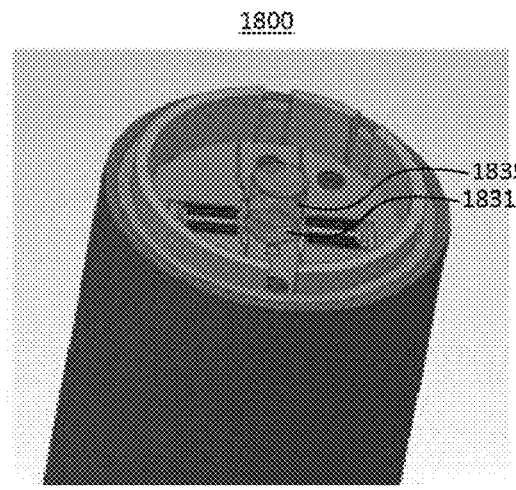
FIG. 19A shows a three dimensional view of the device depicted in FIG. 18.
Figure 19B:
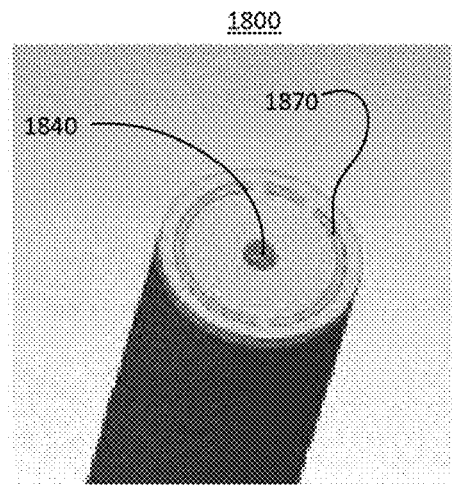
FIG. 19B shows an external view of the device depicted in FIG. 18.
Figure 24:
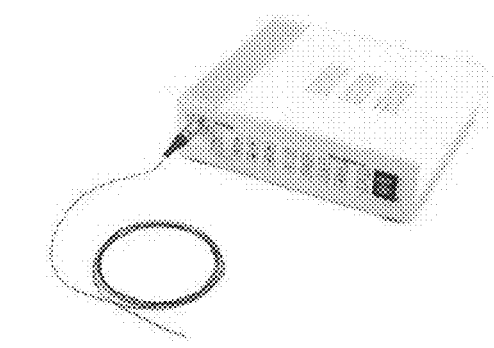
FIG. 24 shows a photo of a 1.1 mm diameter Medigus camera and the camera interface.

FIG. 18 shows a miniature sensor 1800 based on the use of a miniature camera. MediGus and Awaiba GmbH have introduced the world's smallest cameras with diameters of 1.1 mm or less. FIG. 34 is a front view of the sensor 1800. FIG. 24 shows a photo of a 1.1 mm diameter Medigus camera and the camera interface. Incorporation of such cameras into the sensor may allow for improved image quality. As shown in FIG. 18, micro CCD camera 1820 is positioned behind a MEMS-based translating lens device 1830 (i.e., a MEMS plate). The micro CCD camera 1820 may be surrounded by a camera ferrule 1823. The translating lens device 1830 has a translating lens 1831 that directs light micro CCD camera 1820. A window 1840 is used to seal the front end of the sensor 1800. An objective lens 1835 may be positioned between the window 1840 and the translating lens 1831 to improve optical performance. Electrical energy to control the translating lens device 1830 is carried to the device 1830 by wires 1835. The sensor may also contain additional optical fibers 1870 that provide illumination to the area being imaged. An outer sleeve 1810 surrounds all of the interior components to protect those components from damage. As discussed above in regard to FIG. 5, images are captured by the camera 1820 for processing and display. FIG. 19A shows a three dimensional view of the device 1800 depicted in FIG. 18. The objective lens 1835 and the translating lens 1831 are specifically shown in FIG. 19A. FIG. 19B shows an external view of the device 1800 depicted in FIG. 18. The window 1840 and the illuminating fibers 1870 are seen in this view. In this configuration, the lens device may have a diameter of 2.5 mm or less, resulting in the sensor 1800 having a diameter of 3.5 mm or less. Other sensors configured as shown in FIG. 18 may have components (e.g., lens device 1830, camera 1820, etc.) that are sized to result in the sensors having diameters larger than 3.5 mm.

Figure 25:
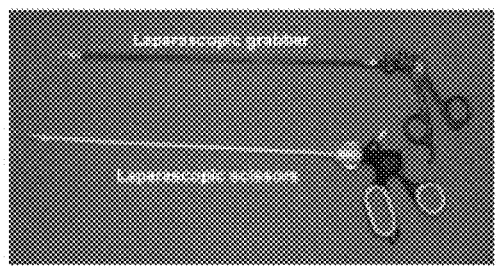
FIG. 25 is a photograph of a laparoscopic grabber and laparoscopic scissors.
Figure 26:
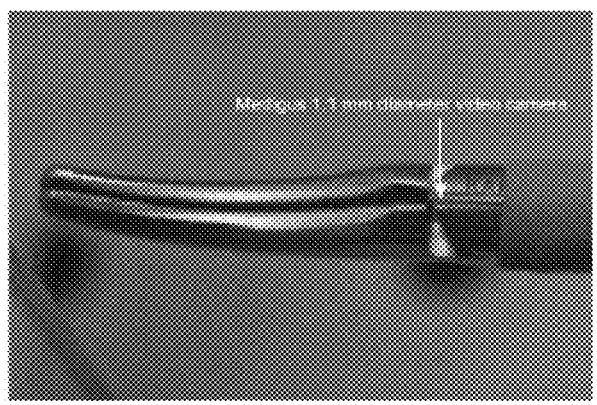
FIG. 26 shows the Medigus 1.1 mm diameter video camera coupled to a grabber.
Figure 27A:
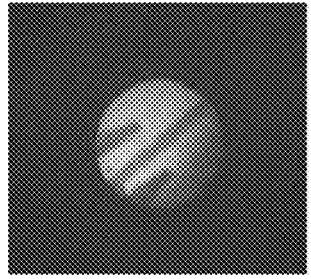
FIGS. 27A and 27B shows images from the Medigus 1.1 mm diameter video camera coupled to the grabber as depicted in FIG. 26.
Figure 27B:
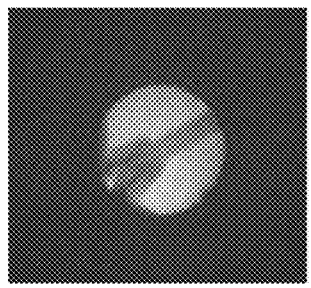
Figure 30:
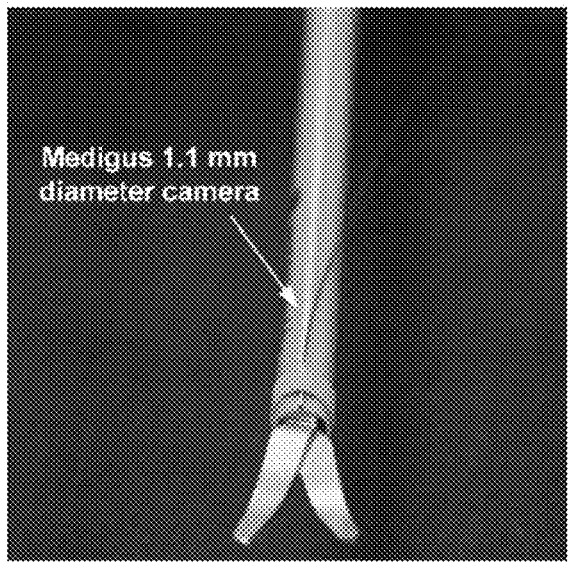
FIG. 30 shows the Medigus 1.1 mm diameter video camera coupled to laparoscopic scissors.
Figure 31:
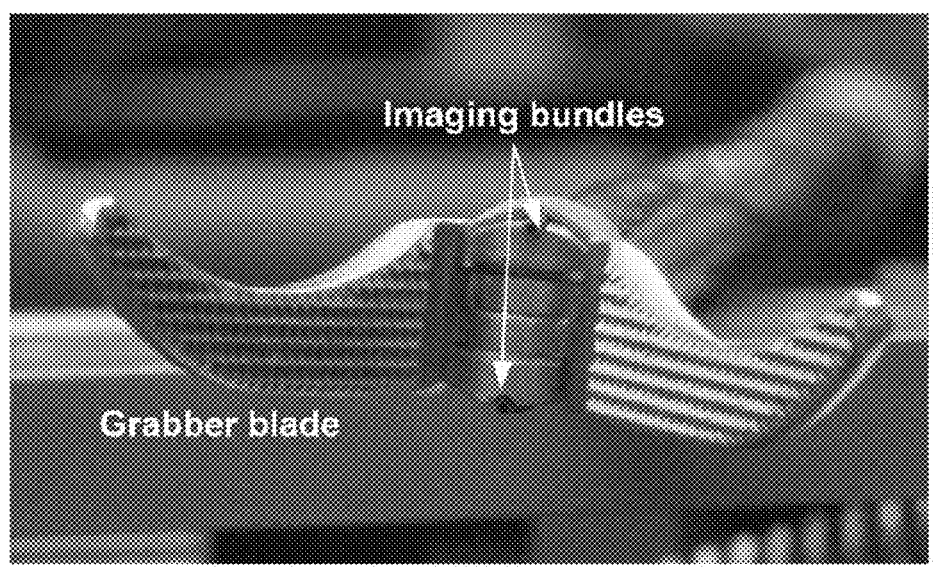
FIG. 31 shows two imaging bundles coupled to a grabber.

Given the foregoing, it is recognized that in diverse surgical procedures of the type that can benefit by the embodiments herein described, depending on the particular surgical activity that is desired to be viewed different distances are of interest. In some cases a shorter distance is desired and in some cases a longer distance is desired. The range over which this variation extends is considered to be from about 3 mm to about 35 mm. For the apparatus and methods disclosed herein, it is considered that to allow working at given portions of the overall working distance, focal length selection can be less than 1 mm and more particularly in the range of about 0.35 mm to about 0.65 mm with a selected aperture in front of the lens of about 0.35 mm to about 0.65 mm As discussed above, the translating lens devices disclosed herein are easily adaptable for use with surgical instruments. Such surgical instruments include, but are not limited to, the laparoscopic grabber and laparoscopic scissors shown in the photograph of FIG. 25. FIG. 26 shows the Medigus 1.1 mm diameter video camera coupled to a grabber. FIG. 30 shows the Medigus 1.1 mm diameter video camera coupled to laparoscopic scissors. Those skilled in the art understand that due to the small form factor of the translating lens devices disclosed herein, such devices can be similarly coupled to a grabber or to scissors. FIG. 27A is an image obtained from the Medigus camera on the grabber of the grabber tips approaching a phantom blood vessel and FIG. 27B is an image of the instrument grabbing the blood vessel also obtained from the Medigus camera. Similar images may be obtained from a translating lens device coupled to a grabber with an additional benefit of obtaining a three dimensional image due to lens translation as described herein. Note also that fiber bundles (such as those described for use in the device 1700 shown in FIG. 17) may also be coupled to surgical instruments. FIG. 31 shows two imaging bundles coupled to a grabber. In accordance with the disclosure herein, those imaging bundles may be replaced with the translating lens devices described herein.

Figure 20:
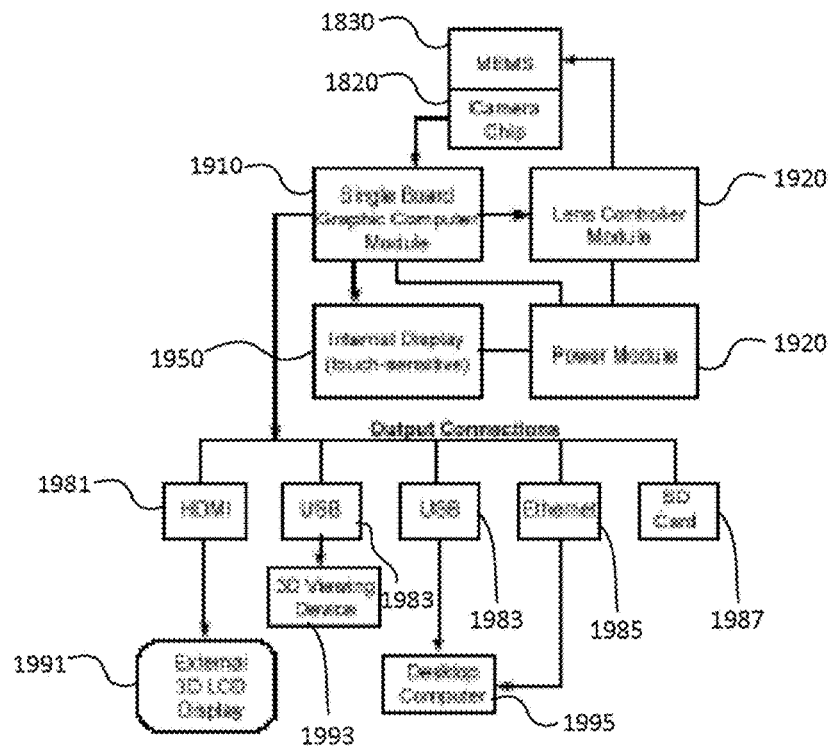
FIG. 20 shows a block diagram for a control system design for a 3D system using a translating lens device and a micro CCD camera.

FIG. 20 shows a block diagram for a control system design for a 3D system using a translating lens device and a micro CCD camera. As shown in FIG. 20, the major electronic components of the system are the video camera 1820, a signal generator/power supply 1930 that powers the translating lens device 1830 (a sinusoidal signal may be used to power the actuators in the device 1830), a lens controller module 1920 for synchronizing camera frame grabbing with the lens movement, and a video processor 1910 (e.g., a single board graphic computer module) to manage the video data stream, computer, and display. As discussed above in regard to FIG. 18, the translating lens device 1830 is optically coupled to the micro CCD camera 1820. A lens control module 1920 controls the translation of the translating lens in the translating lens device 1830. The video processor 1910 receives the video date from the camera 1810 for processing and sends video data to a display 1950. The display 1950 may be touch-sensitive to allow for easy control of the system. The video processor 1910 also provides the trigger to the lens control module 1920 for synchronization. The video processor 1910 may have several output connections (e.g., HDMI 1981, USB 1983, Ethernet 1985, and SD card 1987) to allow for transfer of data to other systems. These output connections may support an external 3D LCD display 1991, another 3D viewing device 1993, or a desktop computer 1995.

To perform the functions discussed above, the video processor 1910 may have application software that is partitioned into several computer software components (CSCs). Table 2 below presents a list of some of the CSCs that may be contained within the application software that runs on the video processor. The application software may contain additional CSCs not listed below.

TABLE 2

| CSC Name | Description |
| --- | --- |
| Initialization CSC | Initialize DRAM memory. Read configuration parameter values and tables from flash into DRAM for access by the program. Initialize and run a brief diagnostic on all of the unit's peripherals. Run a diagnostic on the Computer Module's processor and memory. Start operation if and when warm-up completes successfully. |
| Database CSC | Maintain the system's database, including code to read configuration parameters from flash on device startup into DRAM memory, changing configuration parameters upon request from the Operator Console CSC, and saving configuration parameters upon command to the SD card. |
| Video Input CSC | Control and process images from the camera in the Computer Module's built-in hardware and application software to decode, color correct, filter and enhance incoming images from the camera. The output of this CSC is an RGB image stored in one of two DRAM video image buffers |
| Video Output CSC | For every pair of frames received from the camera, calculate the shift, create and enhance a corresponding 3D image, generate the color-coded distance map and write it to the display thru the video output processing logic on the Computer Module. |
| Operator Display CSC | Control operation of the touch screen display by detecting touches on the touch-sensitive screen and taking the required actions to respond to such commands. |
| Logging CSC | Write the Event Log, 3D Image Log, and/or the Distance Map Log (if any or all are selected for logging) to files on the SD card, a USB port, or the Ethernet port. |
| Diagnostic CSC | Perform diagnostics requested by executing one or a sequence of tests to identify hardware malfunctions and/or to validate correct operation of particular components of the system. |

Figure 21:
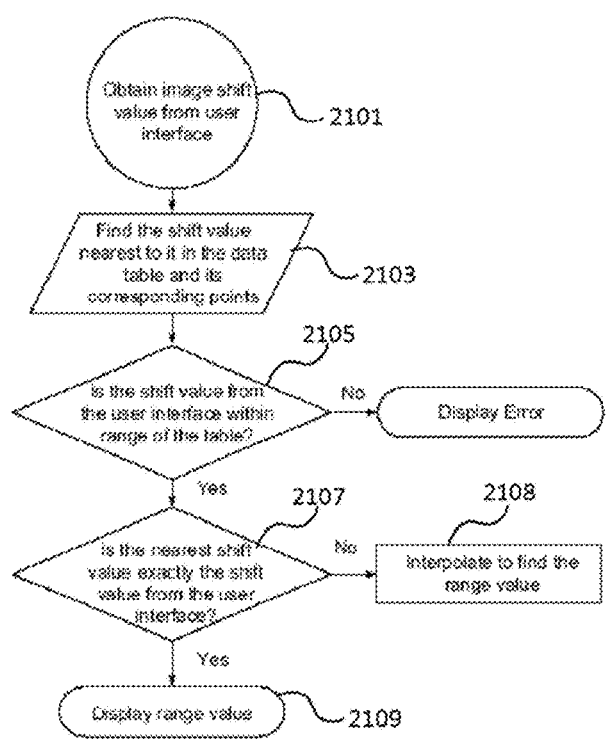
FIG. 21 shows a flow chart for software used for range finding.

As discussed above, one capability provided by the translating lens device is the ability to measure distances to objects within the images. That is, the range from the imaging device or an instrument coupled to the device to a displayed object can be determined. This will support a surgeon in tracking an instrument in very tight or crowded environments, when performing a LESS or NOTES procedure. An optical method for tracking the instrument measuring range allows for passive range that is a non-contact method that can be used at such short distances and in such crowded environments. Traditional laser rangefinder will not work under the LESS or NOTES conditions since it is inaccurate at short distances and the area from which the beam reflects is uncertain. The same is true of ultrasonic methods. The optical range finding capability can be extremely useful to a surgeon performing laparoscopic or endoscopic surgery, since range indications will assist in the manipulation of surgical instruments. FIG. 21 shows a flow chart for software used for range finding. Step 2101 shows that image shift data may be obtained from the images provided by a translated lens. Step 2103 shows that the shift value is used in a look up table. The look-up table may comprise a table similar to Table 1 above that maps shifts values to ranges. Step 2105 determines of the shift value is within the look-up table. Step 2107 determines if the exact value is within the table. If not, step 2108 shows that an interpolation is performed to find the range value. Step 2109 shows that the determined range value is then displayed. Note that equations may be used in place of the look-up table described above.

Figure 22:
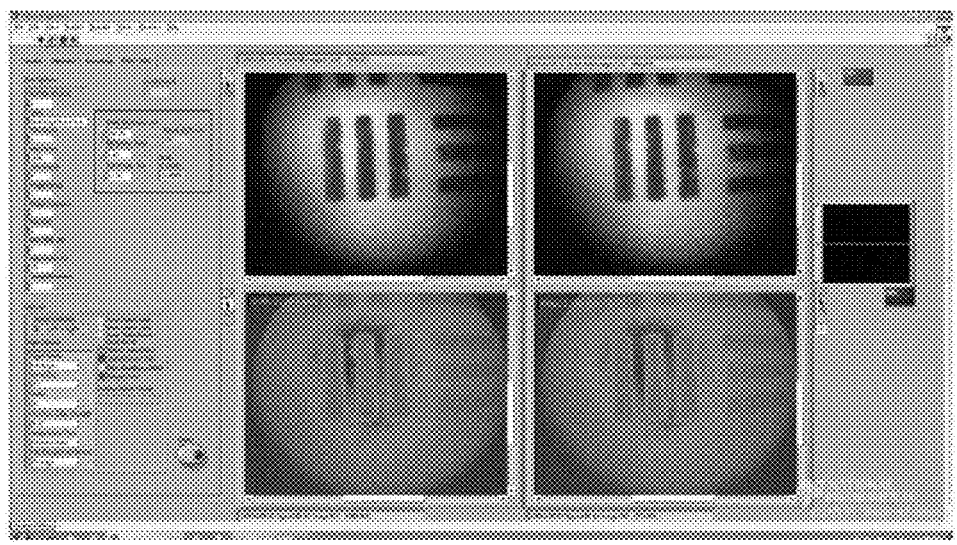
FIG. 22 shows a user interface for control of range finding.
Figure 35:
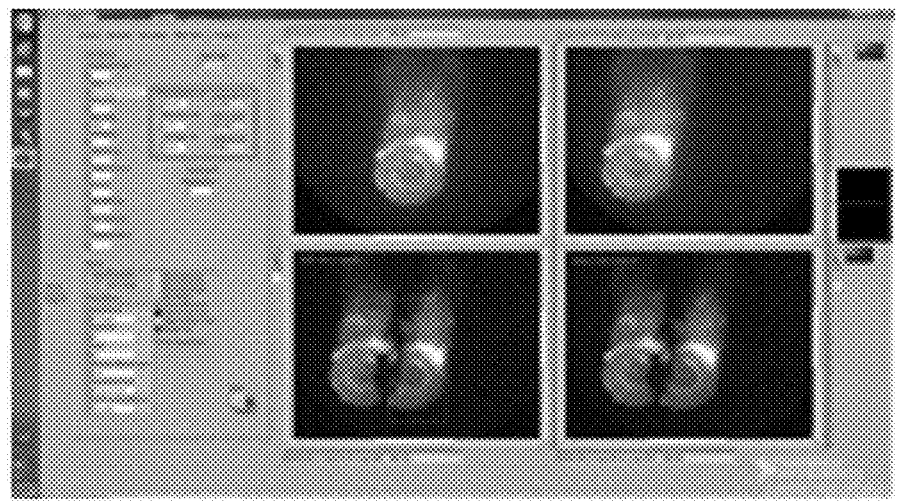
FIG. 35 shows a user interface for range finding showing images of a pipette tip.

Control of range finding may be provided through a user interface, such as that shown in FIGS. 22 and 35. FIG. 22 shows images of a test pattern, while FIG. 35 shows images of a pipette tip. In FIGS. 22 and 35, controls are on the left side of the screen. The middle part of the screen is divided into four segments. The right and the left images (related to two opposite positions of the translating lens) are displayed on the upper segments. The image shift (light gray line on the side of the test strips) is shown in the left bottom segment. This shift is also displayed in the bottom right (measuring) segment. To measure the distance between two points on the object, a user clicks at the beginning point and at the end point. To measure the area, a user surrounds the area by clicking at one point of the edge and then dragging the mouse around the area of interest. The software will automatically conduct measurements and the result will be displayed on the right bottom screen (text in the left upper corner of the right bottom screen). Those skilled in the art understand that other user interfaces may also be used to control range finding and display range or distance data.

Figure 36A:
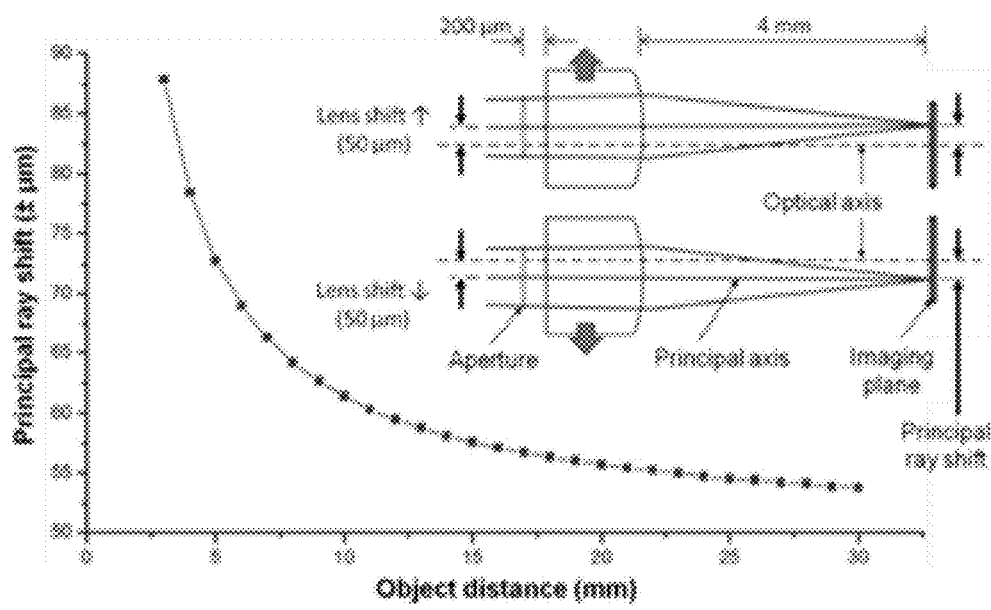

FIGS. 36A-36F illustrate the processing used for distance measurement. FIG. 36A shows a graph of the image shift versus distance to an object based on a lens translation of ±50 μm (as shown by the diagram in the upper left hand corner of FIG. 36A). FIGS. 36B and 36C show two different images of the same object that result from the translated lens being shifted to a first maximum extent of +50 μm and the a second maximum extent of −50 μm. These images would appear, for example, in the upper right and left segments of the user interface shown in FIGS. 22 and 35. FIG. 36D shows the overlapped shifted images from FIGS. 36B and 36C. This image would appear, for example, in the left bottom segment of the user interface shown in FIGS. 22 and 35. The shift can then be highlighted by clicking to signify a shift area (as shown by the box in FIG. 36D). A program could then calculate the shift in pixels as shown in FIG. 36E. A program could then use the pixel shift information along with the shift versus distance data represented by the graph in FIG. 36A to calculate the distance to the object. The result of this calculation is shown by the display box shown in FIG. 36F, which could be placed in the top left side of the user interface shown in FIGS. 22 and 35.

Figure 23:
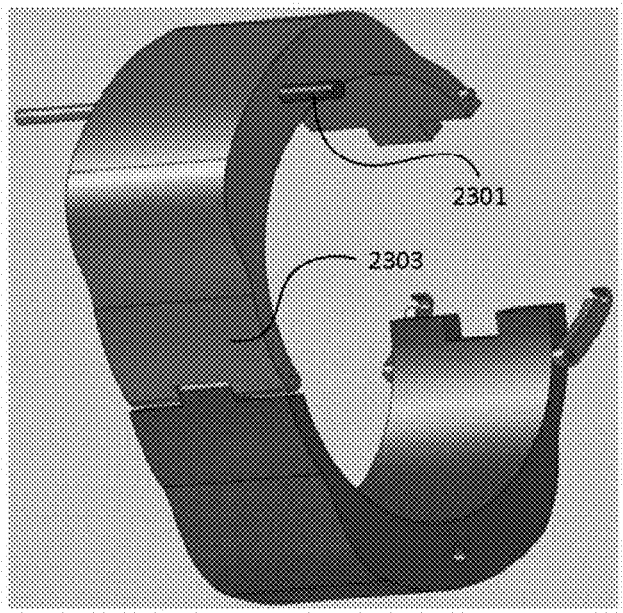
FIG. 23 shows a clamp that may be used to clamp a translating lens device to a surgical instrument.

As briefly discussed above, the translating lens device may be configured to allow for its attachment to any surgical instrument. FIG. 23 shows a clamp 2303 that may be used to clamp the translating lens device 2301 to a surgical instrument. The clamp 2303 may have an overall diameter of 4 mm when uses to clamp a translating lens device with a diameter of 3.5 mm. Other clamps would have different sizes depending upon the lens device to be clamped and/or the tool to which the lens device is to be clamped. Of course, other clamp configurations or other devices or methods may be used to attach translating lens devices to surgical instruments.

The devices, systems, and methods disclosed herein provide a single imaging system that can be used to observe an object in 3D and measure the distance to the object by different viewing angles simply by translating the lens, without using either multiple lens systems which inevitably increases the system size and structural complexity, or one or more off-axis apertures which would generate dark images. The disclosed devices, systems, and methods do not require a multiple lens system for stereo-image acquisition. A single translating lens reduces overall device size and structural complexity, and is especially beneficial in endoscopic applications where size of the tool is a main concern. The disclosed devices, systems, and methods achieve variable viewpoints by gradually translating the lens instead of having two fixed imaging channels as in conventional stereo-imaging systems. With the low manufacturing cost and structural simplicity by not having multiple lens systems (e.g., multiple cameras, lenses, or optical circuits), disclosed devices, systems, and methods can be easily equipped (i.e., by attaching an actuator to translate a lens in an objective lens group) to turn conventional optical systems into one with stereo imaging capabilities. Note also that the translating lens may be kept in a fixed position to provide standard 2 dimensional viewing of an object or area. Thus the expense of providing a multiple imaging systems for 2D and 3D viewing is avoided.

The foregoing Detailed Description of exemplary and preferred embodiments is presented for purposes of illustration and disclosure in accordance with the requirements of the law. It is not intended to be exhaustive nor to limit the invention to the precise form or forms described, but only to enable others skilled in the art to understand how the invention may be suited for a particular use or implementation. The possibility of modifications and variations will be apparent to practitioners skilled in the art.

No limitation is intended by the description of exemplary embodiments which may have included tolerances, feature dimensions, specific operating conditions, engineering specifications, or the like, and which may vary between implementations or with changes to the state of the art, and no limitation should be implied therefrom. In particular it is to be understood that the disclosures are not limited to particular compositions or biological systems, which can, of course, vary. This disclosure has been made with respect to the current state of the art, but also contemplates advancements and that adaptations in the future may take into consideration of those advancements, namely in accordance with the then current state of the art. It is intended that the scope of the invention be defined by the Claims as written and equivalents as applicable. It is also to be understood that the terminology used herein is for the purpose of describing particular embodiments only, and is not intended to be limiting. Reference to a claim element in the singular is not intended to mean "one and only one" unless explicitly so stated. As used in this specification and the appended claims, the singular forms "a," "an," and "the" include plural referents unless the content clearly dictates otherwise. The term "several" includes two or more referents unless the content clearly dictates otherwise. Unless defined otherwise, all technical and scientific terms used herein have the same meaning as commonly understood by one of ordinary skill in the art to which the disclosure pertains.

Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising step(s) for . . . "

A number of embodiments of the disclosure have been described. Nevertheless, it will be understood that various modifications may be made without departing from the spirit and scope of the present disclosure. Accordingly, other embodiments are within the scope of the following claims.

What is claimed is:

1. A method for tracking a surgical instrument during internal surgery, the method comprising:
providing a video sensor configured to image an observed area containing at least a portion of the surgical instrument and an area around the surgical instrument;
directing light from the observed area through a lens to the video sensor, wherein the lens is at a first linear extent and wherein the video sensor captures a first image;
translating the lens in a linear direction to a second linear extent, wherein δ is a lens translating distance defined by a distance between the first linear extent and the second linear extent;
directing light from the observed area through the lens at the second linear extent to the video sensor, wherein the video sensor captures a second image;
processing the first image and the second image to estimate a position of the surgical instrument relative to the area around the surgical instrument, wherein the track of the surgical instrument is based upon the position estimate; and
establishing the track of the surgical instrument based upon the position estimate, and
wherein an image shift Δ between the first image and the second image is equal to $\delta \times (\gamma+1)$ where $\gamma$ is a magnification of an object related to a distance of the object from the lens.

2. The method according to claim 1, wherein processing the first image and the second image to estimate a position comprises processing the first image and the second image to produce a stereo image of the observed area and establishing the track of the surgical instrument comprises viewing the stereo image.

3. The method according to claim 1, wherein the lens is housed in a device attached to the surgical instrument.

4. The method according to claim 1, wherein processing the first image and the second image to estimate a position of the surgical instrument comprises:
calculating a shift value for a reference point on an object within the observed area between the first image and the second image; and
calculating a distance to the object based on the shift value.

5. The method according to claim 4, further comprising: providing an alert based on the calculated distance.

6. A method for tracking a surgical instrument during internal surgery, the method comprising:
providing a surgical instrument;
providing a surgical instrument guide attached to the surgical instrument; wherein the surgical instrument guide has a MEMS translation lens optical system providing an image shift;
providing a video sensor configured to image an observed area containing at least a portion of the surgical instrument and an area around the surgical instrument;
directing light from the observed area through the MEMS translation lens optical system to the video sensor, wherein the MEMS translation lens optical system is at a first linear extent and wherein the video sensor captures a first image;
translating the MEMS translation lens optical system in a linear direction to a second linear extent;
directing light from the observed area through the MEMS translation lens optical system at the second linear extent to the video sensor, wherein the video sensor captures a second image;
processing the first image and the second image to estimate a position of the surgical instrument relative to the area around the surgical instrument, wherein the track of the surgical instrument is based upon the position estimate; and
establishing the track of the surgical instrument based upon the position estimate,
and wherein the MEMS translation lens optical system provides an image shift according to the following equation:

$$\text{visible image shift } \Delta = \delta \times (\gamma+1)$$

where δ is a physical shift distance of a translating lens relative to an optical axis of the MEMS translation lens optical system in the MEMS translation portion; and
where γ is a magnification of an object related to a distance of the object from the translating lens.

7. The method of claim 6, said surgical instrument having means for displaying a 3-D image of the observed area, said image optionally including the surgical instrument or portions thereof and/or portions of an operational field.

8. A method for tracking a surgical instrument during internal surgery, the method comprising:
providing a video sensor configured to image an observed area containing at least a portion of the surgical instrument and an area around the surgical instrument;
directing light from the observed area through a lens to the video sensor, wherein the lens is at a first linear extent and wherein the video sensor captures a first image;
translating the lens in a linear direction to a second linear extent;
directing light from the observed area through the lens at the second linear extent to the video sensor, wherein the video sensor captures a second image;
processing the first image and the second image to estimate a position of the surgical instrument relative to the area around the surgical instrument, wherein the track of the surgical instrument is based upon the position estimate; and
establishing the track of the surgical instrument based upon the position estimate,
wherein the lens has an optical axis and wherein translating the lens in a linear direction comprises translating the lens in a direction transverse to the optical axis.

9. The method according to claim 8, wherein processing the first image and the second image to estimate a position comprises processing the first image and the second image to produce a stereo image of the observed area and establishing the track of the surgical instrument comprises viewing the stereo image.

10. The method according to claim 8, wherein the lens is housed in a device attached to the surgical instrument.

11. The method according to claim 8, wherein processing the first image and the second image to estimate a position of the surgical instrument comprises:
calculating a shift value for a reference point on an object within the observed area between the first image and the second image; and
calculating a distance to the object based on the shift value.

12. The method according to claim 11, further comprising:
providing an alert based on the calculated distance.

13. The method according to claim 6, wherein processing the first image and the second image to estimate a position comprises processing the first image and the second image to produce a stereo image of the observed area and establishing the track of the surgical instrument comprises viewing the stereo image.

14. The method according to claim 6, wherein the lens is housed in a device attached to the surgical instrument.

15. The method according to claim 6, wherein processing the first image and the second image to estimate a position of the surgical instrument comprises:
   calculating a shift value for a reference point on an object within the observed area between the first image and the second image; and
   calculating a distance to the object based on the shift value.

16. The method according to claim 15, further comprising:
   providing an alert based on the calculated distance.

17. A method for tracking a surgical instrument during internal surgery, the method comprising:
   providing a surgical instrument;
   providing a surgical instrument guide attached to the surgical instrument; wherein the surgical instrument guide has a MEMS translation lens optical system providing an image shift;
   providing a video sensor configured to image an observed area containing at least a portion of the surgical instrument and an area around the surgical instrument;
   directing light from the observed area through the MEMS translation lens optical system to the video sensor, wherein the MEMS translation lens optical system is at a first linear extent and wherein the video sensor captures a first image;
   translating the MEMS translation lens optical system in a linear direction to a second linear extent;
   directing light from the observed area through the MEMS translation lens optical system at the second linear extent to the video sensor, wherein the video sensor captures a second image;
   processing the first image and the second image to estimate a position of the surgical instrument relative to the area around the surgical instrument, wherein the track of the surgical instrument is based upon the position estimate; and
   establishing the track of the surgical instrument based upon the position estimate,
   and wherein the MEMS translation lens optical system has an optical axis wherein translating the lens in a linear direction comprises translating the lens in a direction transverse to the optical axis.

18. The method according to claim 17, wherein processing the first image and the second image to estimate a position comprises processing the first image and the second image to produce a stereo image of the observed area and establishing the track of the surgical instrument comprises viewing the stereo image.

19. The method according to claim 17, wherein the lens is housed in a device attached to the surgical instrument.

20. The method according to claim 18, wherein processing the first image and the second image to estimate a position of the surgical instrument comprises:
   calculating a shift value for a reference point on an object within the observed area between the first image and the second image; and
   calculating a distance to the object based on the shift value.

21. The method according to claim 20, further comprising:
   providing an alert based on the calculated distance.

* * * * *